US008436024B2

(12) United States Patent
Murugan et al.

(10) Patent No.: US 8,436,024 B2
(45) Date of Patent: May 7, 2013

(54) 2-PYRIDONE COMPOUNDS

(75) Inventors: Andiappan Murugan, Bangalore (IN); Lena Kristina Bergstrom, Lund (SE); Anna Kristoffersson, Lund (SE); Martin Lindsjö, Lund (SE); Peter Olof Sjö, Lund (SE); Mark David Ashton, Manchester (GB); Jon Meigh, Manchester (GB)

(73) Assignee: Astrazeneca AB, Alderley Park, Macclesfield, Cheshire (GB)

( * ) Notice: Subject to any disclaimer, the term of this patent is extended or adjusted under 35 U.S.C. 154(b) by 33 days.

(21) Appl. No.: 12/895,995

(22) Filed: Oct. 1, 2010

(65) Prior Publication Data
US 2011/0082155 A1    Apr. 7, 2011

Related U.S. Application Data

(60) Provisional application No. 61/248,081, filed on Oct. 2, 2009.

(51) Int. Cl.
*A61K 31/4439* (2006.01)

(52) U.S. Cl.
USPC ........................... 514/341; 546/275.4

(58) Field of Classification Search ............... 546/275.4
See application file for complete search history.

(56) References Cited

U.S. PATENT DOCUMENTS

| 4,181,658 A | 1/1980 | Hitzel et al. |
| 4,186,200 A | 1/1980 | Kubo et al. |
| 5,441,960 A | 8/1995 | Bernstein et al. |
| 5,521,179 A | 5/1996 | Bernstein et al. |
| 6,028,081 A | 2/2000 | Sada et al. |
| 6,977,266 B2 | 12/2005 | Tada et al. |
| 6,979,690 B2 | 12/2005 | Gymer et al. |
| 2004/0023973 A1 | 2/2004 | Nagato et al. |
| 2004/0082619 A1 | 4/2004 | Tada et al. |
| 2004/0235761 A1 | 11/2004 | Furuta et al. |
| 2005/0101590 A1 | 5/2005 | Yasui et al. |
| 2006/0035938 A1 | 2/2006 | Bladh et al. |
| 2006/0052411 A1 | 3/2006 | Tada et al. |
| 2006/0211695 A1 | 9/2006 | Borzilleri et al. |
| 2006/0270666 A1 | 11/2006 | Bladh et al. |
| 2007/0010551 A1 | 1/2007 | Bladh et al. |
| 2007/0043036 A1 | 2/2007 | Hansen et al. |
| 2007/0202301 A1 | 8/2007 | Taniwaki et al. |
| 2007/0203129 A1 | 8/2007 | Andersson et al. |
| 2007/0213323 A1 | 9/2007 | Imogai et al. |
| 2009/0105239 A1 | 4/2009 | Brimert et al. |
| 2009/0131483 A1 | 5/2009 | Hansen et al. |
| 2009/0131486 A1 | 5/2009 | Hansen et al. |
| 2009/0209555 A1 | 8/2009 | Hansen et al. |
| 2010/0216843 A1 | 8/2010 | Briggner et al. |
| 2010/0280048 A1 | 11/2010 | Ainge et al. |

FOREIGN PATENT DOCUMENTS

| EP | 0008864 A1 | 3/1980 |
| GB | 2383326 A | 6/2003 |
| GB | 2392910 A | 3/2004 |
| JP | 2-152966 A | 6/1990 |
| WO | WO-98/24780 A2 | 6/1998 |
| WO | WO-01/96308 A1 | 12/2001 |
| WO | WO-02/053543 A1 | 7/2002 |
| WO | WO-03/047577 A2 | 6/2003 |
| WO | WO-2004/020410 A2 | 3/2004 |
| WO | WO-2005/080372 A1 | 9/2005 |
| WO | WO-2005/082864 A1 | 9/2005 |
| WO | WO-2006/082412 A2 | 8/2006 |
| WO | WO-2006/116713 A1 | 11/2006 |
| WO | WO-2006/136857 A1 | 12/2006 |
| WO | WO-2007/107706 A2 | 9/2007 |
| WO | WO-2007/129060 A1 | 11/2007 |
| WO | WO-2008/030158 A1 | 3/2008 |
| WO | WO-2008/104752 A1 | 9/2008 |
| WO | WO-2009/058076 A1 | 5/2009 |
| WO | WO-2009/061271 A1 | 5/2009 |
| WO | WO-2010/094964 A1 | 8/2010 |

OTHER PUBLICATIONS

U.S. Appl. No. 12/895,995, Muragan et al.
Ukrainets, IV, et al., "4-Hydroxy-2-quinolones. 23. N-(2-Thiazolyl) amides of 1-substituted 4-hydroxy-2-oxoquinoline-3-carboxylic acids—a new group of potential antiinflammatory drugs" STN International, File CAPLUS, CAPLUS accession No. 1995:456529, Document No. 123:198678, Mar. 31, 1995.
"4-Hydroxycarbostyrils as antiinflammatory and antiallergy agents", STN International, File CAPLUS, CAPLUS accession No. 1990:611864, Document No. 113:211864, Jun. 12, 1990.
Harayama, T., et al., "Hydrolysis Products of Flavins (Isoalloxazines)", *J. Chem. Soc. Perkin Trans. I* (1987), pp. 75-83.
Zeiher, B.G., et al., "Neutrophil elastase and acute lung injury: Prospects for sivelestat and other neutrophil elastase inhibitors as therapeutics," *Crit Care Med* (2002), vol. 30, No. 5 (Suppl.), pp. S281-S287.
Ohbayashi, H., "Neutrophil elastase inhibitors as treatment for COPD," *Expert Opin. Investig. Drugs* (2002), vol. 11, No. 7, pp. 965-980.
Ohbayashi, H., "Novel neutrophil elastase inhibitors as a treatment for neutrophil-predominant inflammatory lung diseases," *The Investigational Drugs Journal* (2002), vol. 5, No. 9, pp. 910-923.
Sato, T., et al., "Neutrophil elastase and cancer," *Surgical Oncology* (2006), vol. 15, pp. 217-222.

(Continued)

Primary Examiner — Brian McDowell
(74) Attorney, Agent, or Firm — Astrazeneca AB

(57) ABSTRACT

The invention provides compounds of formula (I)

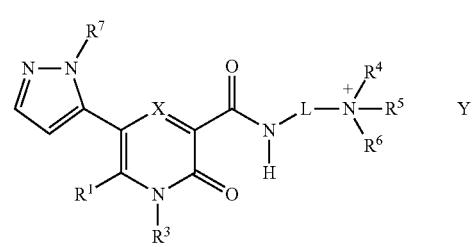

wherein $R^1, R^3, R^4, R^5, R^6, R^7, L, X$ and $Y$ are as defined in the specification; together with processes and intermediates for their preparation, pharmaceutical compositions containing them and their use in therapy. The compounds are inhibitors of human neutrophil elastase.

5 Claims, 2 Drawing Sheets

OTHER PUBLICATIONS

Bauer, A., et al., "1.5-Benzodiazepin-trione und ihre Vorstufen," *Liebigs Ann. Chem.* (1972), vol. 762, pp. 73-82.

Ohbayashi, H., "Current synthetic inhibitors of human neutrophil elastase in 2005," *Expert Opin. Ther. Patents* (2005), vol. 15, No. 7, pp. 759-771.

Fisyuk, A.S. et al., "4-methyl-3,6-diphenyl-5,6-dihydropyridin-2(1H)-one", XP002481053, Beilstein Registry No. 7995731, & KHIM Geterotsikl Soedin vol. 34(1), 1998, pp. 73-76.

Chughtai, B., et al., "Potential Role of Inhibitors of Neutrophil Elastase in Treating Disease of the Airway," *Journal of Aerosol Medicine* (2004), vol. 17, No. 4, pp. 289-298.

"Respiratory experts call for global approach to treat chronic disease", http://www.newtocopd.com/currentaffairsnews/list751_item17680.aspx, Europ. Resp. Soc., Feb. 13, 2007.

Friedman, M., "Future Treatment Strategies for COPD," *Clinical Cornerstone, COPD* (2004), vol. 5, No. 1, pp. 45-51.

Okayama, N., et al., "Clinical effects of a neutrophil elastase inhibitor, sivelestat, in patients with acute respiratory distress syndrome," *J Anesth* (2006), vol. 20, pp. 6-10.

Shimizu, T., et al., "A Mechanism of Antigen-Induced Mucus Production in Nasal Epithelium of Sensitized Rats," *Am J Respir Crit Care Med* (2000), vol. 161, pp. 1648-1654.

Ukrainets, I.V., et al., "4-Hydroxy-2-Quinolones. 23. N-(2-Thiazolyl)amides of 1-R-2-OXO-4-Hydroxyquinoline-3-Carboxylic Acids—A New Group of Potential Antiinflammatory Agents," *Chemistry of Heterocyclic Compounds* (1994), vol. 30, No. 10, pp. 1211-1213.

Wright, J.L., et al., "A neutrophil elastase inhibitor reduces cigarette smoke-induced remodelling of lung vessels," *Eur Respir J* (2003), vol. 22, pp. 77-81.

Office Action dated Apr. 9, 2008; U.S. Appl. No. 10/569,923 (Publication No. 2006-0270666).
Office Action dated Dec. 12, 2008; U.S. Appl. No. 10/569,923 (Publication No. 2006/0270666).
Office Action dated Feb. 28, 2008; U.S. Appl. No. 10/534,720 (Publication No. 2006/0035938).
Office Action dated Jun. 23, 2008; U.S. Appl. No. 10/534,720 (Publication No. 2006/0035938).
Office Action dated Jan. 2, 2009; U.S. Appl. No. 10/534,720 (Publication No. 2006/0035938).
Interview Summary dated Jul. 14, 2009; U.S. Appl. No. 10/534,720 (Publication No. 2006/0035938).
Office Action dated Sep. 29, 2008; U.S. Appl. No. 10/569,571 (Publication No. 2007/0010551).
Office Action dated Mar. 16, 2009; U.S. Appl. No. 10/569,571 (Publication No. 2007/0010551).
Interview Summary dated Sep. 28, 2009; U.S. Appl. No. 10/569,571 (Publication No. 2007/0010551).
Office Action dated Jan. 21, 2009; U.S. Appl. No. 10/572,640 (Publication No. 2007/0043036).
Interview Summary dated Aug. 4, 2009; U.S. Appl. No. 10/572,640 (Publication No. 2007/0043036).
Office Action dated Aug. 25, 2009; U.S. Appl. No. 12/299,879 (Publication No. 2009/0131486).
Office Action dated Dec. 28, 2009; U.S. Appl. No. 12/299,879 (Publication No. 2009/0131486).
Office Action dated Jun. 24, 2010; U.S. Appl. No. 12/299,879 (Publication No. 2009/0131486).
Notice of Allowance and Interview Summary dated Sep. 23, 2010; U.S. Appl. No. 12/299,879 (Publication No. 2009/0131486).
Eistert, B., et al., "Synthese und Reaktionen substituierter Pyrrolin-2,3-dione mit Diazoalkanen," *Liebigs Ann. Chem.* (1976), pp. 1023-1030.

2-PYRIDONE COMPOUNDS

CROSS REFERENCE TO RELATED APPLICATIONS

The present application claims benefit under 35 U.S.C. §119(e) of U.S. Provisional Application Ser. No. 61/248,081 filed on Oct. 2, 2009.

FIELD OF THE INVENTION

The present invention relates to quaternary 2-pyridone derivatives, processes and intermediates for their preparation, pharmaceutical compositions containing them and their use in therapy.

BACKGROUND OF THE INVENTION

Elastases are possibly the most destructive enzymes in the body, having the ability to degrade virtually all connective tissue components. The uncontrolled proteolytic degradation by elastases has been implicated in a number of pathological conditions. Human neutrophil elastase (hNE), a member of the chymotrypsin superfamily of serine proteases is a 33-KDa enzyme stored in the azurophilic granules of the neutrophils. In neutrophils the concentration of NE exceeded 5 mM and its total cellular amount has been estimated to be up to 3 pg. Upon activation, NE is rapidly released from the granules into the extracellular space with some portion remaining bound to neutrophil plasma membrane (See Kawabat et al. 2002, Eur. J. Pharmacol. 451, 1-10). The main intracellular physiological function of NE is degradation of foreign organic molecules phagocytosed by neutrophils, whereas the main target for extracellular elastase is elastin (Janoff and Scherer, 1968, J. Exp. Med. 128, 1137-1155). NE is unique, as compared to other proteases (for example, proteinase 3) in that it has the ability to degrade almost all extracellular matrix and key plasma proteins (See Kawabat et al., 2002, Eur. J. Pharmacol. 451, 1-10). It degrades a wide range of extracellular matrix proteins such as elastin, Type 3 and type 4 collagens, laminin, fibronectin, cytokines, etc. (Ohbayashi, H., 2002, Expert Opin. Investig. Drugs, 11, 965-980). NE is a major common mediator of many pathological changes seen in chronic lung disease including epithelial damage (Stockley, R. A. 1994, Am. J. Resp. Crit. Care Med. 150, 109-113).

The destructive role of NE was solidified almost 40 years ago when Laurell and Eriksson reported an association of chronic airflow obstruction and emphysema with deficiency of serum $\alpha_1$-antitrypsin (Laurell and Eriksson, 1963, Scand. J. Clin. Invest. 15, 132-140). Subsequently it was determined that $\alpha_1$-antitrypsin is the most important endogenous inhibitor of human NE. The imbalance between human NE and endogenous antiprotease is believed to cause excess human NE in pulmonary tissues which is considered as a major pathogenic factor in chronic obstructive pulmonary disease (COPD). The excessive human NE shows a prominent destructive profile and actively takes part in destroying the normal pulmonary structures, followed by the irreversible enlargement of the respiratory airspaces, as seen mainly in emphysema. There is an increase in neutrophil recruitment into the lungs which is associated with increased lung elastase burden and emphysema in $\alpha_1$-proteinase inhibitor-deficient mice (Cavarra et al., 1996, Lab. Invest. 75, 273-280). Individuals with higher levels of the NE-$\alpha_1$ protease inhibitor complex in bronchoalveolar lavage fluid show significantly accelerated decline in lung functions compared to those with lower levels (Betsuyaku et al. 2000, Respiration, 67, 261-267). Instillation of human NE via the trachea in rats causes lung haemorrhage, neutrophil accumulation during acute phase and emphysematous changes during chronic phase (Karaki et al., 2002, Am. J. Resp. Crit. Care Med., 166, 496-500). Studies have shown that the acute phase of pulmonary emphysema and pulmonary haemorrhage caused by NE in hamsters can be inhibited by pre-treatment with inhibitors of NE (Fujie et al., 1999, Inflamm. Res. 48, 160-167).

Neutrophil-predominant airway inflammation and mucus obstruction of the airways are major pathologic features of COPD, including cystic fibrosis and chronic bronchitis. NE impairs mucin production, leading to mucus obstruction of the airways. NE is reported to increase the expression of major respiratory mucin gene, MUCSAC (Fischer, B. M & Voynow, 2002, Am. J. Respir. Cell Biol., 26, 447-452). Aerosol administration of NE to guinea pigs produces extensive epithelial damage within 20 minutes of contact (Suzuki et al., 1996, Am. J. Resp. Crit. Care Med., 153, 1405-1411). Furthermore NE reduces the ciliary beat frequency of human respiratory epithelium in vitro (Smallman et al., 1984, Thorax, 39, 663-667) which is consistent with the reduced mucociliary clearance that is seen in COPD patients (Currie et al., 1984, Thorax, 42, 126-130). The instillation of NE into the airways leads to mucus gland hyperplasia in hamsters (Lucey et al., 1985, Am. Resp. Crit. Care Med., 132, 362-366). A role for NE is also implicated in mucus hypersecretion in asthma. In an allergen sensitised guinea pig acute asthma model an inhibitor of NE prevented goblet cell degranulation and mucus hypersecretion (Nadel et al., 1999, Eur. Resp. J., 13, 190-196).

NE has been also shown to play a role in the pathogenesis of pulmonary fibrosis. NE: $\alpha_1$-protenase inhibitor complex is increased in serum of patients with pulmonary fibrosis, which correlates with the clinical parameters in these patients (Yamanouchi et al., 1998, Eur. Resp. J. 11, 120-125). In a murine model of human pulmonary fibrosis, a NE inhibitor reduced bleomycin-induced pulmonary fibrosis (Taooka et al., 1997, Am. J. Resp. Crit. Care Med., 156, 260-265). Furthermore investigators have shown that NE deficient mice are resistant to bleomycin-induced pulmonary fibrosis (Dunsmore et al., 2001, Chest, 120, 35S-36S). Plasma NE level was found to be elevated in patients who progressed to ARDS implicating the importance of NE in early ARDS disease pathogenesis. (Donnelly et al., 1995, Am. J. Res. Crit. Care Med., 151, 428-1433). The antiproteases and NE complexed with antiprotease are increased in lung cancer area (Marchandise et al., 1989, Eur. Resp. J. 2, 623-629). Recent studies have shown that polymorphism in the promoter region of the NE gene are associated with lung cancer development (Taniguchi et al., 2002, Clin. Cancer Res., 8, 1115-1120.

Acute lung injury caused by endotoxin in experimental animals is associated with elevated levels of NE (Kawabata, et al., 1999, Am. J. Resp. Crit. Care, 161, 2013-2018). Acute lung inflammation caused by intratracheal injection of lipopolysaccharide in mice has been shown to elevate the NE activity in bronchoalveolar lavage fluid which is significantly inhibited by a NE inhibitor (Fujie et al., 1999, Eur. J. Pharmacol., 374, 117-125; Yasui, et al., 1995, Eur. Resp. J., 8, 1293-1299). NE also plays an important role in the neutrophil-induced increase of pulmonary microvascular permeability observed in a model of acute lung injury caused by tumour necrosis factor $\alpha$ (TNF$\alpha$) and phorbol myristate acetate (PMA) in isolated perfused rabbit lungs (Miyazaki et al., 1998, Am. J. Respir. Crit. Care Med., 157, 89-94).

A role for NE has also been suggested in monocrotoline-induced puhnonary vascular wall thickening and cardiac hypertrophy (Molteni et al., 1989, Biochemical Pharmacol.

38, 2411-2419). Serine elastase inhibitor reverses the monocrotaline-induced pulmonary hypertension and remodelling in rat pulmonary arteries (Cowan et al., 2000, Nature Medicine, 6, 698-702). Recent studies have shown that serine elastase, that is, NE or vascular elastase are important in cigarette smoke-induced muscularisation of small pulmonary arteries in guinea pigs (Wright et al., 2002, Am. J. Respir. Crit. Care Med., 166, 954-960).

NE plays a key role in experimental cerebral ischemic damage (Shimakura et al., 2000, Brain Research, 858, 55-60), ischemia-reperfusion lung injury (Kishima et al., 1998, Ann Thorac. Surg. 65, 913-918) and myocardial ischemia in rat heart (Tiefenbacher et al., 1997, Eur. J. Physiol., 433, 563-570). Human NE levels in plasma are significantly increased above normal in inflammatory bowel diseases, for example, Crohn's disease and ulcerative colitis (Adeyemi et al., 1985, Gut, 26, 1306-1311). In addition NE has also been assumed to be involved in the pathogenesis of rheumatoid arthritis (Adeyemi et al., 1986, Rheumatol. Int., 6, 57). The development of collagen induced arthritis in mice is suppressed by a NE inhibitor (Kakimoto et al., 1995, Cellular Immunol. 165, 26-32).

Thus, human NE is known as one of the most destructive serine proteases and has been implicated in a variety of inflammatory diseases. The important endogenous inhibitor of human NE is $\alpha_1$-antitrypsin. The imbalance between human NE and antiprotease is believed to give rise to an excess of human NE resulting in uncontrolled tissue destruction. The protease/antiprotease balance may be upset by a decreased availability of $\alpha_1$-antitrypsin either through inactivation by oxidants such as cigarette smoke, or as a result of genetic inability to produce sufficient serum levels.

Human NE has been implicated in the promotion or exacerbation of a number of diseases such as adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis or gastric mucosal injury. Particular conditions include for example, pulmonary emphysema, pulmonary fibrosis, adult respiratory distress syndrome (ARDS), ischemia reperfusion injury, rheumatoid arthritis and pulmonary hypertension.

Alpha-1-antitrypsin deficiency (AATD) is a hereditary genetic disorder which results in low serum levels of alpha-1 antitrypsin. Patients with AATD are prone to develop a number of diseases including lung disease such as emphysema and COPD, liver disease such as cirrhosis and the skin disease panniculitis. Patients with AATD are particularly prone to develop lung diseases such as COPD and emphysema. These conditions are likely to be accelerated when patients with AATD are exposed to environmental factors such as cigarette smoking, and dust exposure. A number of treatments for AATD have been approved including Prolastin®, Araslast®, Zemaira®. These treatments are all proteins which are administered to patients intravenously to increase the levels of alpha-1-antitrypsin, or derivatives thereof, in the serum. However, there remains a need to identify alternative treatments for patients with AATD.

WO 2005/026123, WO 2007/107706, WO 2007/129962, WO 2007/129963, WO 2008/030158 disclose certain 2-pyridone and 2-pyrazinone derivatives useful as inhibitors of human neutrophil elastase. The present application discloses 2-pyridone and 2-pyrazinone derivatives which carry a quaternary ammonium substituent. The compounds are potent inhibitors of human neutrophil elastase and also possess advantageous DMPK and physical properties such as good solubility. In particular, the compounds have properties that make them particularly suited to administration by inhalation. For example certain compounds are expected to exhibit a high retention in the lung following inhalation.

DISCLOSURE OF THE INVENTION

Figure 1:
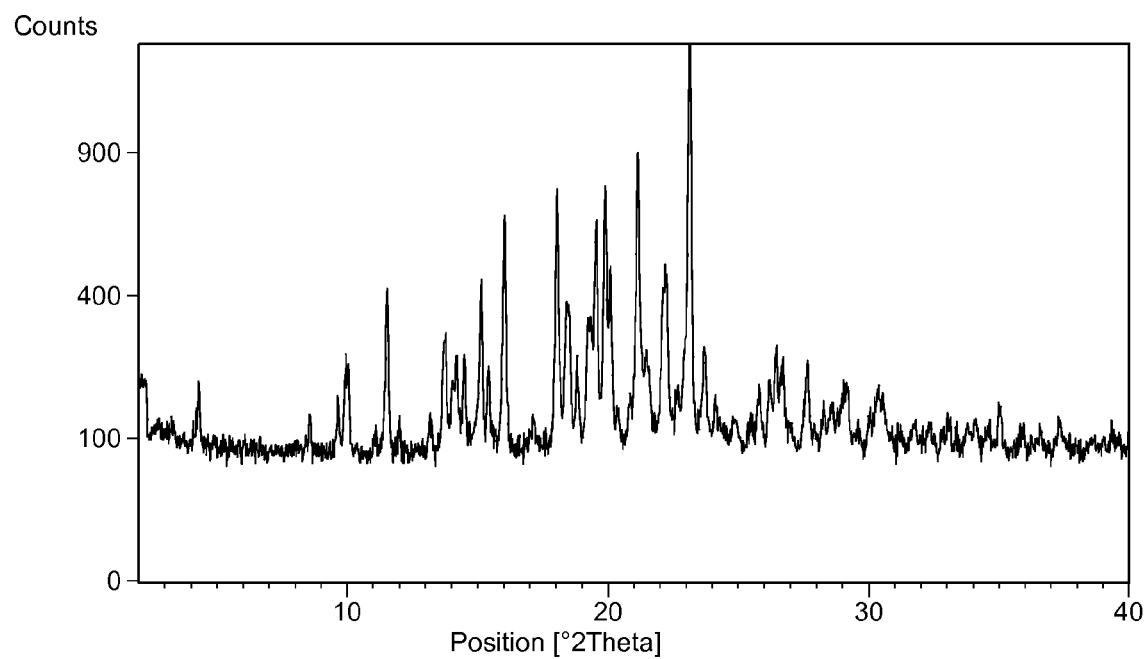
FIG. 1 is an X-ray powder diffraction diagram of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form A measured using CuKα1 radiation (1.5406 Å, 45 kV, 40 mA). The x-axis shows the 2-theta value and the y-axis the intensity.

In accordance with the present invention, there is therefore provided a compound of formula (I):

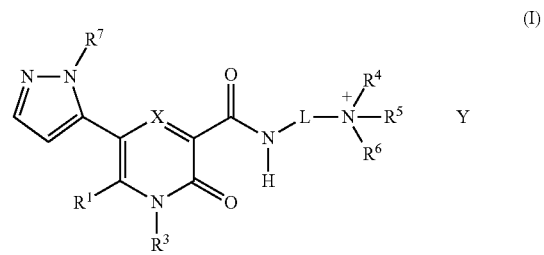

(I)

wherein $R^1$ represents hydrogen or $C_1$-$C_4$ alkyl;

$R^7$ represents phenyl or pyridinyl ring, said ring being 4-(para) substituted with fluoro, chloro or CN;

X represents N or $CR^2$ wherein $R^2$ represents H or fluoro;

$R^3$ represents a phenyl group substituted with one or two substituents independently selected from fluoro, chloro and trifluoromethyl;

L represents $C_2$-$C_4$ alkylene;

$R^4$, $R^5$ and $R^6$ each independently represent $C_1$-$C_6$ alkyl; or $R^4$ and $R^5$ may be joined together such that the group $NR^4R^5$ together represents a 5- or 6-membered cyclic ammonium group; and Y represents a pharmaceutically acceptable anion.

In the context of the present specification, unless otherwise stated, an alkyl moiety may be linear or branched, but references to individual alkyl groups such as "propyl" are specific for the straight chain version only. Similarly, an alkylene group may be linear or branched. Examples of $C_1$-$C_4$ alkyl include methyl, ethyl, propyl and isopropyl; examples of $C_1$-$C_6$ alkyl include methyl, ethyl, propyl, isopropyl, t-butyl, pentyl, iso-pentyl, 1-2-dimethylpropyl and hexyl; examples of $C_1$-$C_2$ alkyl include ethyl, propyl, isopropyl, t-butyl.

When $R^4$ and $R^5$ are joined together such that the group $NR^4R^5$ together represents a 5- or 6-membered cyclic ammonium group, the cyclic group so formed is a nitrogen-linked quaternised 5- or 6-membered heterocyclyl group. For example $NR^4R^5$ together form a quaternised nitrogen-linked 5 or 6 membered ring, which is a saturated or partially saturated non-aromatic heterocyclyl ring containing 1 nitrogen and optionally 1, 2 or 3 heteroatoms selected from oxygen, sulfur and nitrogen (but not containing any O—O, O—S or S—S bonds), and wherein the ring so formed is linked via a ring nitrogen atom to the group L in formula (I). For example $NR^4R^5$ may form, for example a quaternised 2-pyrrolin-1-yl, 3-pyrrolin-1-yl, pyrrolidin-1-yl, imidazolidin-1-yl, piperidino, piperazin-1-yl, morpholino or thiomorpholino group. In one embodiment $NR^4R^5$ together form a quaternised pyrrolidin-1-yl, piperidino, morpholino or thiomorpholino group. In another embodiment $NR^4R^5$ together form a quaternised pyrrolidin-1-yl, piperidino, morpholino group, more particularly a quaternised pyrrolidin-1-yl or piperidino group. In another embodiment $NR^4R^5$ together form a quaternised pyrrolidin-1-yl group. As will be realised, when $R^4$ and $R^5$ joined together such that the group $NR^4R^5$ together represents a 5- or 6-membered cyclic ammonium group, the nitrogen of the ring is quaternised by the group $R^6$ which represents represent $C_1$-$C_6$ alkyl, such as methyl or ethyl, particularly methyl.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibit of human neutrophil elastase and is not to be limited merely to any one tautomeric form utilised within the formulae drawings.

It is also to be understood that certain compounds of the formula (I) and salts thereof can exist in solvated as well as unsolvated forms such as, for example, hydrated forms. It is to be understood that the invention encompasses all such solvated forms which inhibit human neutrophil elastase. Some compounds of the formula (I) may exhibit polymorphism. It is to be understood that the present invention encompasses any such polymorphic form, or mixtures thereof, which form possesses properties useful in the inhibition of human neutrophil elastase.

$R^1$ represents hydrogen or $C_1$-$C_4$ alkyl (e.g. methyl, ethyl, n-propyl, isopropyl, n-butyl, isobutyl or tert-butyl).

In one embodiment of the invention, $R^1$ represents a $C_1$-$C_2$ alkyl group, in particular a methyl group.

$R^7$ represents phenyl or pyridinyl; said ring being 4-(para) substituted with fluoro, chloro or CN.

In one embodiment, $R^7$ represents phenyl 4-(para) substituted with fluoro, chloro or CN. In one embodiment, $R^7$ represents phenyl 4-(para) substituted with CN.

X represents N or CH or CF. In one embodiment, X represents N. In one embodiment, X represents CH.

$R^3$ represents a phenyl group substituted with one or two substituents independently selected from fluorine, chlorine, cyano and trifluoromethyl.

In one embodiment, $R^3$ represents a phenyl group substituted with a trifluoromethyl substituent. In another embodiment $R^3$ is represents a phenyl group substituted in the 3-(meta) position with trifluoromethyl.

In another embodiment, $R^3$ represents a phenyl group substituted in the 3-(meta) position with bromo, chloro, trifluoromethyl or CN.

L represents a linear or branched $C_2$-$C_4$ alkylene (e.g. $C_2$ alkylene, $C_3$ alkylene or $C_4$ alkylene). In one embodiment, L represents a linear $C_2$-$C_4$ alkylene (—$CH_2CH_2$—, —$CH_2CH_2CH_2$— or —$CH_2CH_2CH_2CH_2$—).

In one embodiment of the invention, L represents linear $C_3$ alkylene (trimethylene (n-propylene)). In one embodiment of the invention, L represents —$CH_2CH_2$—. In another embodiment L represents —$CH_2CH_2CH_2$—. In another embodiment L represents -$CH_2CH_2$ $_{CH2}$ $CH_2$—.

$R^4$, $R^5$ and $R^6$ independently represent $C_1$-$C_6$ alkyl (e.g. methyl, ethyl, n-propyl, isopropyl, n-butyl, isobutyl, tert-butyl, pentyl or hexyl); or $R^4$ and $R^5$ may be joined together such that the group $NR^4R^5$ together represents a 5- or 6-membered cyclic ammonium group (e.g. pyrrolidinium or piperidinium).

In one embodiment, $R^4$, $R^5$ and $R^6$ each independently represent $C_1$-$C_6$ or $C_1$-$C_4$ or $C_1$-$C_2$ alkyl.

In another embodiment, $R^4$, $R^5$ and $R^6$ each independently represent $C_1$-$C_2$ alkyl, for example a methyl group.

In another embodiment, $NR^4R^5$ together represents a 5- or 6-membered cyclic ammonium group. In a further embodiment $NR^4R^5$ together represents a pyrrolidinium group. In a further embodiment $NR^4R^5$ together represents a piperidinium group.

In another embodiment, $NR^4R^5$ together represents a 5- or 6-membered cyclic ammonium group (e.g. pyrrolidinium or piperidinium and particularly pyrrolidinium) and $R^6$ represents $C_1$-$C_2$ alkyl, for example a methyl group.

In one aspect of the invention, there is provided a compound of formula (I) wherein:
$R^1$ represents a $C_1$-$C_2$ alkyl group, for example a methyl group;
$R^7$ represents phenyl 4-(para) substituted with fluoro, chloro or CN;
X represents CH;
$R^3$ represents a phenyl group substituted in the 3-(meta) position with bromo, chloro, trifluoromethyl or CN;
L represents $C_2$-$C_4$ alkylene;
$R^4$, $R^5$ and $R^6$ independently represent $C_1$-$C_6$ alkyl; and
Y represents a pharmaceutically acceptable anion.

In another embodiment of the invention, there is provided a compound of formula (I) wherein:
$R^1$ represents a methyl group;
$R^7$ represents phenyl 4-(para) substituted with fluoro, chloro or CN;
X represents CH;
$R^3$ represents a phenyl group substituted in the 3-(meta) position with trifluoromethyl;
L represents $C_2$-$C_4$ alkylene;
$R^4$, $R^5$ and $R^6$ each independently represent $C_1$-$C_4$ alkyl; and
Y represents a pharmaceutically acceptable anion.

In another embodiment of the invention, there is provided a compound of formula (I) wherein:
$R^1$ represents a methyl group;
$R^7$ represents phenyl 4-(para) substituted with CN;
X represents CH;
$R^3$ represents a phenyl group substituted in the 3-(meta) position with trifluoromethyl;
L represents $C_2$-$C_4$ alkylene;
$R^4$, $R^5$ and $R^6$ each independently represent $C_1$-$C_2$ alkyl; and
Y represents a pharmaceutically acceptable anion.

In another embodiment of the invention, there is provided a compound of formula (I) wherein:
$R^1$ represents a methyl group;
$R^7$ represents phenyl 4-(para) substituted with CN;
X represents CH;
$R^3$ represents a phenyl group substituted in the 3-(meta) position with trifluoromethyl;

L represents —CH$_2$CH$_2$ CH$_2$— or —CH$_2$CH$_2$ CH$_2$—;

R$^4$, R$^5$ and R$^6$ each independently represent methyl or ethyl (for example methyl); and Y represents a pharmaceutically acceptable anion.

In another embodiment of the invention, there is provided a compound of formula (I) wherein:

R$^1$ represents a methyl group;

R$^7$ represents phenyl 4-(para) substituted with CN;

X represents CH;

R$^3$ represents a phenyl group substituted in the 3-(meta) position with trifluoromethyl;

L represents C$_2$-C$_4$ alkylene;

R$^4$ and R$^5$ are joined together such that the group NR$^4$R$^5$ together represents a 5 or 6 membered cyclic ammonium group (for example pyrrolidinium);

R$^6$ represents C$_1$-C$_2$ alkyl; and

Y represents a pharmaceutically acceptable anion.

A particular compound of the invention is a compound selected from List A:

List A

1-{2-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]ethyl}-1-methylpyrrolidinium Y;

1-{4-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]butyl}-1-methylpyrrolidinium Y;

2-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]-N,N,N-trimethylethanaminium Y;

4-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]-N,N,N-trimethylbutan-1-aminium Y;

1-{3-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]propyl}-1-methylpyrrolidinium Y;

3-[({6-[1-(4-cyanophenyl)-1H-pyrazol-5-yl]-5-methyl-3-oxo-4-[3-(trifluoromethyl)phenyl]-3,4-dihydropyrazin-2-yl}carbonyl)amino]-N,N,N-trimethylpropan-1-aminium Y; and 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium Y;

wherein Y represents a pharmaceutically acceptable anion.

In another embodiment of the invention there is provided a compound of the formula (I), which is 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium Y, wherein Y represents a pharmaceutically acceptable anion.

In another embodiment of the invention there is provided a compound according to formula (I) which is any one of the Examples described herein.

In another embodiment of the invention there is provided a compound of the formula (I) other than any one of the compounds according to List A.

In another embodiment of the invention there is provided a compound of the formula (I) selected from List A other than any one of the compounds in the Examples. Accordingly, in one embodiment there is provided a compound of the formula (I) (for example a compound selected from List A) other than 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate (besylate). In another embodiment of the invention there is provided a compound of the formula (I) (for example selected from List A) other than 3-[({6-[1-(4-cyanophenyl)-1H-pyrazol-5-yl]-5-methyl-3-oxo-4-[3-(trifluoromethyl)phenyl]-3,4-dihydropyrazin-2-yl}carbonyl)amino]-N,N,N-trimethylpropan-1-aminium iodide. In another embodiment of the invention there is provided a compound of the formula (I) (for example selected from List A) other than 3-[({6-[1-(4-cyanophenyl)-1H-pyrazol-5-yl]-5-methyl-3-oxo-4-[3-(trifluoromethyl)phenyl]-3,4-dihydropyrazin-2-yl}carbonyl)amino]-N,N,N-trimethylpropan-1-aminium acetate.

The compounds of formula (I) comprise a pharmaceutically acceptable anion Y associated with the positive charge on the quaternary nitrogen atom. The anion Y may be any pharmaceutically acceptable anion of a mono or polyvalent (e.g. bivalent) acid. As will be realised when Y is polyvalent for example a divalent anion Y$^{2-}$ the compound of formula (I) may form a hemi-salt with the divalent anion of the formula:

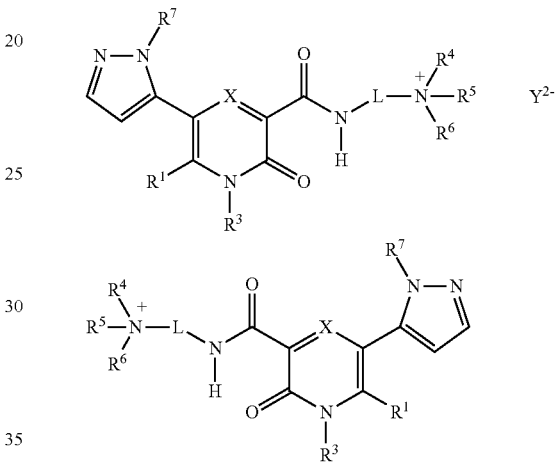

In an embodiment of the invention Y may be an anion of a mineral acid, for example chloride, bromide, iodide, sulfate, nitrate or phosphate; or an anion of a suitable organic acid, for example acetate, maleate, fumarate, citrate, oxalate, succinate, tartrate, saccharinate, cinnamate, mandelate, lactate, malonate, malate, methane sulphonate (mesylate), p-toluenesulphonate, benzenesulfonate, napadisylate (naphthalene-1, 5-disulphonate) (e.g. a heminapadisylate), 1-hydroxy-2-naphthoate, 1-hydroxynaphthalene-2-sulphonate. In another embodiment Y represents, for example, halide, acetate, mesylate or benzenesulfonate. In one embodiment of the invention Y represents halide, for example chloride, bromide or iodide. In another embodiment Y represents iodide. In another embodiment Y represents bromide. In another embodiment Y represents chloride. In another embodiment Y represents acetate. In another embodiment Y represents mesylate. In another embodiment Y represents benzenesulfonate (besylate). The specific pharmaceutically acceptable anions Y described herein may be associated with any of the embodiments described herein, for example any of the compounds described in List A hereinbefore. Certain anions (Y) provide compounds with advantageous properties. For example the compound 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate is crystalline and exhibits good physical properties, such as low hygroscopicity.

As mentioned hereinbefore some compounds of the formula (I) according to the invention may exhibit polymorphism. Polymorphism can be characterised as the ability of a particular compound to crystallise in different crystal modifications whilst maintaining the same chemical formula. Polymorphs of a given substance are chemically identical in containing the same atoms bonded to one another in the same way, but differ in their crystal modifications, which can affect one or more physical properties such as dissolution rate, melting point, bulk density, stability, flow properties, etc. As used in the specification with reference to a specific compound, the terms "polymorph", "crystal modification", "crystal form", "crystalline modification" and "(crystalline) Form" are to be understood as synonymous.

According to one embodiment of the invention there is provided a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form A.

3-(5-(1-(4-Cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form A is crystalline and provides an X-ray powder diffraction (XRPD) pattern substantially as shown in FIG. 1 when measured using CuKα1 radiation (1.5406 Å, 45 kV, 40 mA) as described in the Examples. The most prominent peaks (2θ value) of Form A are shown in Table 1.

TABLE 1

| Angle 2-Theta (2θ)° |
| --- |
| 4.3 |
| 11.5 |
| 13.7 |
| 14.5 |
| 15.1 |
| 15.4 |
| 16.0 |
| 18.0 |
| 18.8 |
| 19.5 |
| 19.9 |
| 20.1 |
| 21.1 |
| 23.1 |
| 23.7 |

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form A, characterised in that said Form A has an X-ray powder diffraction (XPRD) pattern with specific peaks at 4.3 and 23.1 °2θ when measured using CuKα1 radiation (1.5406 Å, 45 kV, 40 mA).

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form A, characterised in that said Form A has an X-ray powder diffraction (XPRD) pattern with specific peaks at 4.3, 11.5 and 23.1 °2θ when measured using CuKα1 radiation (1.5406 Å, 45 kV, 40 mA).

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form A, characterised in that said Form A has an X-ray powder diffraction (XPRD) pattern with specific peaks at 4.3, 11.5, 13.7, 21.1 and 23.1°2θ when said XPRD pattern is measured using CuKα1 radiation (1.5406 Å, 45 kV, 40 mA).

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form A, characterised in that said Form A has an X-ray powder diffraction (XPRD) pattern with specific peaks at 4.3, 11.5, 13.7, 18.0, 19.9, 21.1 and 23.1°2θ when measured using CuKα1 radiation (1.5406 Å, 45 kV, 40 mA).

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form A, characterised in that said Form A has an X-ray powder diffraction (XPRD) pattern substantially as shown in FIG. 1 when said XPRD pattern is measured using CuKα1 radiation (1.5406 Å, 45 kV, 40 mA).

According to one embodiment of the invention there is provided a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form B.

Figure 2:
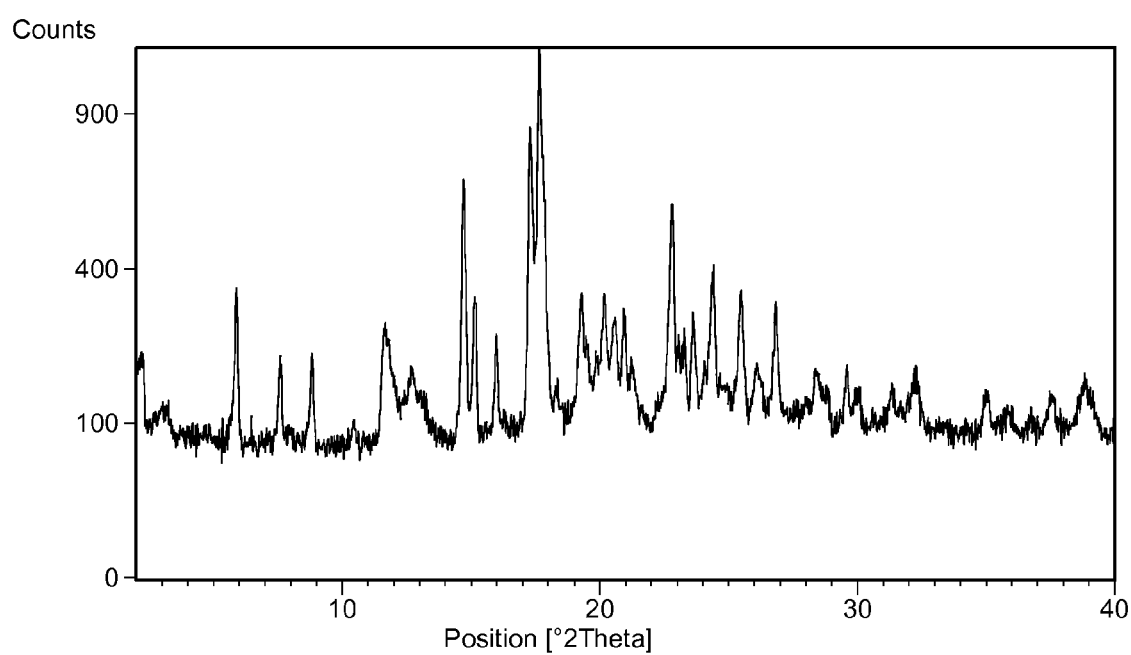
FIG. 2 is an X-ray powder diffraction diagram of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form B measured using CuKα1 radiation (1.5406 Å, 45 kV, 40 mA). The x-axis shows the 2-theta value and the y-axis the intensity.

3-(5-(1-(4-Cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form B is crystalline and provides an X-ray powder diffraction (XRPD) pattern substantially as shown in FIG. 2 when measured using CuKα1 radiation (1.5406 Å, 45 kV, 40 mA) as described in the Examples. The most prominent peaks (2θ value) of Form B are shown in Table 2.

TABLE 2

| Angle 2-Theta (2θ)° |
| --- |
| 5.8 |
| 7.5 |
| 8.7 |
| 14.6 |
| 15.1 |
| 15.9 |
| 17.2 |
| 17.6 |
| 19.2 |
| 22.7 |
| 23.6 |
| 24.3 |
| 25.4 |
| 26.8 |

The crystalline modification 3-(5-(1-(4-Cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form B has good physical properties including low hygroscopicity and is thought to be more thermodynamically stable than Form A hereinbefore described. As such Form B is expected to be particularly suitable for use in the preparation of pharmaceutical compositions for use in therapy.

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form B, characterised in that said Form B has an X-ray powder diffraction (XPRD) pattern with specific peaks at 5.8 and 17.2°2θ and when measured using CuKα1 radiation (1.5406 Å, 45 kV, 40 mA).

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form B, characterised in that said Form B has an X-ray powder diffraction (XPRD) pattern with specific peaks at 5.8, 7.5 and 17.2 °2θ when measured using CuKα1 radiation (1.5406 Å, 45 kV, 40 mA).

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form B, characterised in that said Form B has an X-ray powder diffraction (XPRD) pattern with specific peaks at 5.8, 7.5, 8.7, 17.2 and 24.3 °2θ and when measured using CuKα1 radiation (1.5406 Å, 45 kV, 40 mA).

In another embodiment, the invention provides a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form B, characterised in that said Form B has an X-ray powder diffraction (XPRD) pattern with specific peaks at 5.8, 7.5, 8.7, 17.2, 17.6, 22.7, 24.3 and 25.4 °2θ when measured using CuKα1 radiation (1.5406 Å, 45 kV, 40 mA).

In another embodiment, the invention provides a crystalline modification of a crystalline modification of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form B, characterised in that said Form B has an X-ray powder diffraction (XPRD) pattern substantially as shown in FIG. 2 when said XPRD pattern is measured using CuKα1 radiation (1.5406 Å, 45 kV, 40 mA).

Suitably a crystalline modification of a compound according to the invention is substantially free from other crystalline modifications of the compound. Suitably, a described crystalline modification of a compound of the formula (I) suitably includes less than 20%, 15%, 10%, 5%, 3% or particularly, less than 1% by weight of other crystalline, and non-crystalline forms of that compound. For example the 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form B is suitably substantially free from Form A of the compound. Similarly Form A of that compound is suitably substantially free from Form B of the compound.

When herein reference is made to a compound according to the invention being crystalline, such as 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated as Form A or Form B, suitably the degree of crystallinity as determined by X-ray powder diffraction data, is for example greater than about 60%, such as greater than about 80%, particularly greater than about 90%, more particularly greater than about 95%. In embodiments of the invention, the degree of crystallinity as determined by X-ray powder diffraction data is greater than about 98%, wherein the % crystallinity refers to the % by weight of the total sample mass which is crystalline.

In the preceding paragraphs defining the X-ray powder diffraction peaks for the crystalline forms of compounds according to the invention the 2θ values should not be construed as being absolute values because, as will be appreciated by those skilled in the art, the precise position of the peaks may vary slightly between one measurement apparatus and another, from one sample to another, or as a result of slight variations in measurement conditions utilised. It is also stated in the preceding paragraphs that 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate designated Forms A and B provide X-ray powder diffraction patterns 'substantially' the same as the X-ray powder diffraction patterns shown in FIGS. 1 and 2 respectively, and has substantially the most prominent peaks (2θ angle values) shown in Tables 1 and 2. It is to be understood that the use of the term 'substantially' in this context is also intended to indicate that the 2θ angle values of the X-ray powder diffraction patterns may vary slightly from one apparatus to another, from one sample to another, or as a result of slight variations in measurement conditions utilised, so the peak positions shown in the Figures or quoted in the Tables are again not to be construed as absolute values.

The person skilled in the art of X-ray powder diffraction will realize that the relative intensity of peaks can be affected by, for example, grains above approximately 30 micrometer in size and non-unitary aspect ratios which may affect analysis of samples. Furthermore, it should be understood that intensities may fluctuate depending on experimental conditions and sample preparation such as preferred orientation of the particles in the sample. The use of automatic or fixed divergence slits will also influence the relative intensity calculations. A person skilled in the art can handle such effects when comparing diffraction patterns.

The person skilled in the art of X-ray powder diffraction will also realize that due to difference in sample heights and errors in the calibration of the detector position, a small shift in the 2θ positions could occur. Generally, a difference of ±0.2° from the given value are to be considered correct. These error tolerances equate to typically a sample height difference of 1 mm.

The crystalline modifications of the compounds described herein may also be characterised and/or distinguished from other physical forms using other suitable analytical techniques, for example NIR spectroscopy or solid-state nuclear magnetic resonance spectroscopy. The chemical structure of a compound according to the invention can be confirmed by routine methods for example proton nuclear magnetic resonance (NMR) analysis.

In a further aspect the present invention also provides that the compounds of the formula (I) and salts thereof, can be prepared by a process (a) as follows (wherein all variables are as hereinbefore defined for a compound of formula (I) unless otherwise stated, except any functional group is protected if required):

(a) reacting a compound of the formula (II):

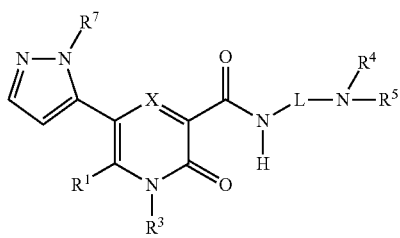

with a compound of the formula (III):

R⁶—Y                                            (III)

and thereafter optionally:
i) removing any protecting groups; and/or
ii) forming a pharmaceutically acceptable salt with a pharmaceutically acceptable anion;

wherein $R^1$, $R^3$, $R^4$, $R^5$, $R^6$, $R^7$, L and Y are as hereinbefore defined, or $R^4$ and $R^5$ may be joined together such that the group $NR^4R^5$ together represents a 5- or 6-membered cyclic group.

Process (a) Conditions

In process (a), when Y is iodide, the reaction may conveniently be carried out in the presence of a suitable solvent for example a polar aprotic solvent such as acetonitrile or acetone. The reaction is suitably carried out at a temperature in the range of from ambient to about 70° C., for example about 55° C. When Y is bromide the reaction with an alkyl bromide such as methyl bromide is suitably carried out in a high pressure reactor at a temperature of ambient temperature to about 150° C., for example about 70° C.

Compounds of formula (II) may be prepared by, for example, reacting a compound of the formula (IV):

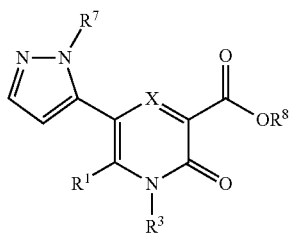

wherein $R^8$ is $C_1$-$C_6$ alkyl (for example $C_1$-$C_4$ alkyl such as methyl or ethyl); with an amine of the formula (V):

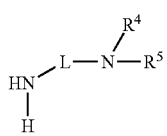

The reaction is suitably performed in the presence of a suitable solvent such as an alcohol, for example methanol or ethanol. The reaction is suitably carried out at a temperature of from about 50 to 150° C., for example, about the reflux temperature.

Compounds of the formulae (III) and (V) are known or can be made by routine methods in the art.

Compounds of the formula (IV) where X is N are known and can be made by for example, analogous methods to those described in WO2009/061271. Compounds of the formula (N) wherein X is CH may be prepared using analogous methods to those described in the Examples for the synthesis of Intermediate A. For example by coupling a compound of the formula (VI) with a compound of the formula (VII):

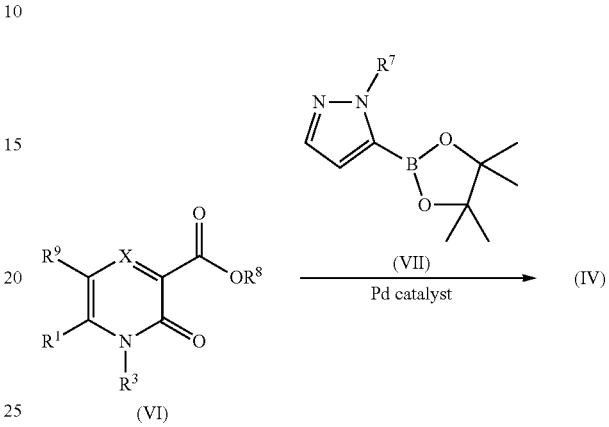

wherein $R^9$ is halo (for example iodo).

Alternatively, compounds of the formula (II) may be prepared by coupling a compound of the formula (VIII):

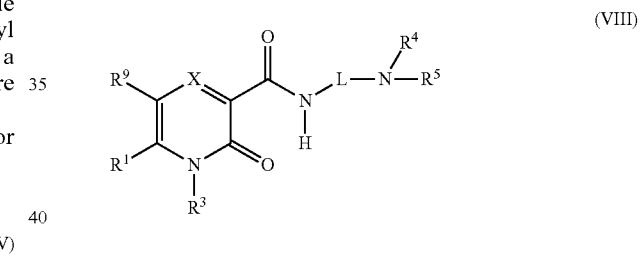

wherein $R^9$ is halo (for example iodo) with a compound of the formula (VII) as hereinbefore defined.

The coupling of the compounds of formulae (VI) and (VII) and the compounds of formulae (VIII) and (VII) are performed in the presence of a suitable base and catalyst. Examples of suitable bases include an inorganic or organic base. Suitable inorganic bases include for example, a carbonate such as potassium carbonate, a phosphate such as potassium phosphate dibasic ($K_2HPO_3$) or potassium phosphate tribasic ($K_2PO_4$) or a hydroxide base such as barium, sodium or potassium hydroxide. Suitable organic bases include an organic amine such as triethylamine or N-diisopropylethylamine (Hunigs base), or an alkali metal bases such as sodium acetate or a sodium alkoxide such as sodium methoxide or sodium ethoxide. The catalyst is suitably a palladium catalyst such as 1,1'-bis(di-tert-butylphosphino) ferrocene palladium dichloride.

The coupling reaction is carried out in the presence of water, for example 1 mole equivalent or 50% v/v as solvent. In addition to the water the reaction is conveniently performed in a suitable solvent, for example dimethylformamide, 2-methyl-tetrahydrofuran, acetonitrile, 1-methyl 2-pyrrolidinone, dimethoxyethane, dioxane, toluene, anisole, an alcohol (for example, ethanol or isopropanol) or an ester (for example, butyl acetate). The reaction is suitably performed at ambient or elevated temperature, for example at about 40° C.

As will be realised, it may be possible to perform the coupling reaction using alternative boronic acids and esters to the specific boronic ester shown in the compound of formula (VII).

Compounds of the formula (VIII) may be prepared by, for example, reacting a compound of the formula (IX), or an activated derivative thereof:

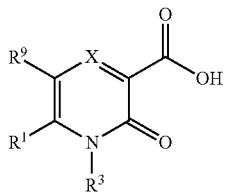

(IX)

with an amine of the formula (V) as hereinbefore defined.

Examples of activated derivatives of the compound of formula (IX) include carboxylic acid derivatives of the compound of formula (IX) suitable for amide formation. Such reactive derivatives could include, for example, an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide, with 1,1'-carbonyl diimidazole, or with a uronium compound such as 2-(7-azabenzotriazol-1-yl)-1,1,3,3-tetramethyluronium hexafluorophosphate(V).

The reaction is conveniently carried out in a suitable solvent or diluent. For example, N,N-dimethylformamide. The reaction is conveniently carried out at a temperature in the range, for example, 0 to 120° C., suitably at or near ambient temperature.

Compounds of the formula (IX) are known or can be prepared using known methods for the preparation of analogous compounds.

Specific processes for the preparation of compounds of formula (I) are disclosed within the Examples section of the present specification. Such processes form an aspect of the present invention.

The necessary starting materials are either commercially available, are known in the literature or may be prepared using known techniques. Specific processes for the preparation of certain key starting materials are disclosed within the Examples section of the present specification and such processes form an aspect of the present invention.

If not commercially available, the necessary starting materials for the procedures such as those described above may be made by procedures which are selected from standard organic chemical techniques, techniques which are analogous to the synthesis of known, structurally similar compounds, techniques which are described or illustrated in the references given above, or techniques which are analogous to the above described procedure or the procedures described in the examples. The reader is further referred to Advanced Organic Chemistry, 5th Edition, by Jerry March and Michael Smith, published by John Wiley & Sons 2001, for general guidance on reaction conditions and reagents.

Certain intermediates used in the preparation of the compounds of formula (I) are novel and form a further aspect of the present invention. More particularly, there is provided a compound of the formula (II) as hereinbefore described.

In particular there is provided a compound of the formula (II), or a salt thereof, as hereinbefore described Examples of compounds of the formula (II) include a compound selected from:

5-[1-(4-cyanophenyl)-1H-pyrazol-5-yl]-6-methyl-2-oxo-N-(2-pyrrolidin-1-ylethyl)-1-[3-(trifluoromethyl)phenyl]-1,2-dihydropyridine-3-carboxamide;

5-[1-(4-cyanophenyl)-1H-pyrazol-5-yl]-6-methyl-2-oxo-N-(3-pyrrolidin-1-ylpropyl)-1-[3-(trifluoromethyl)phenyl]-1,2-dihydropyridine-3-carboxamide;

5-[1-(4-cyanophenyl)-1H-pyrazol-5-yl]-6-methyl-2-oxo-N-(4-pyrrolidin-1-ylbutyl)-1-[3-(trifluoromethyl)phenyl]-1,2-dihydropyridine-3-carboxamide;

5-[1-(4-cyanophenyl)-1H-pyrazol-5-yl]-N-[2-(dimethylamino)ethyl]-6-methyl-2-oxo-1-[3-(trifluoromethyl)phenyl]-1,2-dihydropyridine-3-carboxamide;

5-(1-(4-cyanophenyl)-1H-pyrazol-5-yl)-N-(3-(dimethylamino)propyl)-6-methyl-2-oxo-1-[3-(trifluoromethyl)phenyl]-1,2-dihydropyridine-3-carboxamide; and 5-[1-(4-cyanophenyl)-1H-pyrazol-5-yl]-N-[4-(dimethylamino)butyl]-6-methyl-2-oxo-1-[3-(trifluoromethyl)phenyl]-1,2-dihydropyridine-3-carboxamide;

or a salt thereof.

Another example of a compound of the formula (II) is 6-[1-(4-cyanophenyl)-1H-pyrazol-5-yl]-N-[3-(dimethylamino)propyl]-5-methyl-3-oxo-4-[3-(trifluoromethyl)phenyl]-3,4-dihydropyrazine-2-carboxamide, or a salt thereof.

In a further aspect of the invention there is provided a compound of the formula (VIII'), or a salt thereof:

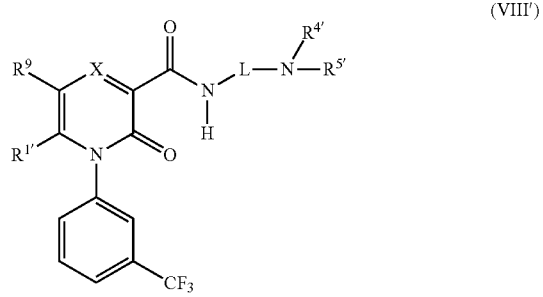

(VIII')

wherein:

$R^{1'}$ represents $C_1$-$C_4$ alkyl (for example methyl);

X represents N or $CR^2$ wherein $R^2$ represents H or fluoro;

L represents $C_2$-$C_4$ alkylene;

$R^{4'}$ and $R^{5'}$ may be joined each independently represent $C_1$-$C_6$ alkyl; or $R^{4'}$ and $R^{5'}$ may be joined together such that the group $NR^{4'}R^{5'}$ together represents a 5 or 6 membered saturated or partially saturated non-aromatic heterocyclyl ring containing 1 nitrogen and optionally 1, 2 or 3 heteroatoms selected from oxygen, sulphur and nitrogen; and $R^9$ is halo (for example iodo);

or a salt thereof.

In one embodiment $R^{4'}$ and $R^{5'}$ each independently represent $C_1$-$C_6$ alkyl, for example methyl or ethyl. In another embodiment $R^{4'}$ and $R^{5'}$ are both methyl.

In another embodiment X in the compound of formula (VIII') is CH.

A particular example of a compound of the formula (VIII') is N-[3-(dimethylamino)propyl]-5-iodo-6-methyl-2-oxo-1-[3-(trifluoromethyl)phenyl]-1,2-dihydropyridine-3-carboxamide, or a salt thereof.

The rings which may be formed by the groups $NR^4R^5$ and $NR^4R^{5'}$ in the compounds of formulae (II) and (VIII') respectively are nitrogen linked to the group L. Examples of such rings include a nitrogen-linked 5 or 6 membered ring, which is a saturated or partially saturated non-aromatic heterocyclyl ring containing 1 nitrogen and optionally 1, 2 or 3 heteroatoms selected from oxygen, sulfur and nitrogen (but not containing any O—O, O—S or S—S bonds), and wherein the ring so formed is linked via a ring nitrogen atom to the group L. For example a 2-pyrrolin-1-yl, 3-pyrrolin-1-yl, pyrrolidin-1-yl, imidazolidin-1-yl, piperidino, piperazin-1-yl, morpholino or thiomorpholino group. In one embodiment said ring is a pyrrolidin-1-yl, piperidino, morpholino or thiomorpholino group. In another embodiment said ring is a pyrrolidin-1-yl, piperidino or morpholino group. In another embodiment said ring is a pyrrolidin-1-yl or piperidino group.

The compounds of formulae (II) and (VIII') may be used in the form of a salt. The salt may be a pharmaceutically acceptable salt, such as one of the salts mentioned hereinbefore in relation to compounds of the formula (I). Alternatively, if required, the compounds of formulae (II) and (VIII') may be used in the form of a salt which is not a pharmaceutically acceptable salt. Such salts may be advantageously used in the synthesis of compounds according to the invention, for example as a result of advantageous physical and/or chemical properties, such as crystallinity.

It will be appreciated by those skilled in the art that in the processes of the present invention certain functional groups such as hydroxyl or amino groups may need to be protected by protecting groups. Thus, the preparation of the compounds of formula (I) may involve, at an appropriate stage, the addition and/or removal of one or more protecting groups.

The protection and deprotection of functional groups is described in 'Protective Groups in Organic Chemistry', edited by J. W. F. McOmie, Plenum Press (1973) and Protective Groups in Organic Synthesis', $3^{rd}$ edition, T. W. Greene and P. G. M. Wuts, Wiley-Interscience (1999).

The removal of any protecting groups and the formation of a pharmaceutically acceptable salt are within the skill of an ordinary organic chemist using standard techniques. For example alternative salts of a compounds of formula (I) may be prepared using well-known counter ion exchange methods. Such salt formation methods may therefore be used to convert a compound of the formula (I) with a particular anion Y to give the compound of formula (I) with a different anion.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The crystalline modifications of 3-(5-(1-(4-cyanophenyl)-1H-pyrazol-5-yl)-6-methyl-2-oxo-1-(3-(trifluoromethyl) phenyl)-1,2-dihydropyridine-3-carboxamido)-N,N,N-trimethylpropan-1-aminium benzenesulfonate Form A and Form B described herein may be prepared by crystallisation from a suitable solvent system as described in the Examples herein, for example by crystallisation from a mixture of isopropanol and ethanol, or acetone and 2-methyltetrahydrofuran. For preparation on a larger scale, seeding may be used to promote the formation of the desired form, for example seeding the reaction mixture with Form B will promote the formation of the Form B crystal modification.

The compounds of formula (I) have activity as pharmaceuticals, in particular as modulators human neutrophil elastase. Accordingly the compounds of formula (I) may be beneficial in the treatment or prophylaxis of inflammatory diseases and conditions, for example those diseases and conditions listed below.

1. Diseases of the respiratory tract such as obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

2. Diseases of bone and joints including: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

3. Pain and connective tissue remodelling of musculoskeletal disorders due to injury [for example, sports injury] or disease including: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis).

4. Diseases of skin including: psoriasis, atopic dermatitis, contact dermatitis or other eczematous dermiatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidennolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

5. Diseases of the eye including: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

6. Diseases of the gastrointestinal tract including: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, non-inflammatory diarrhoea, and food-related allergies which may have effects remote from the gut (for example, migraine, rhinitis or eczema).

7. Diseases of the cardiovascular system including: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins.

8. Oncology including: the treatment of common cancers including prostate, breast, lung, ovarian, pancreatic, bowel and colon, stomach, skin and brain tumours and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

In particular, the compounds of formula (I) may be used in the treatment of adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis and gastric mucosal injury.

More particularly, the compounds of formula (I) may be used in the treatment of chronic obstructive pulmonary disease (COPD), cystic fibrosis, bronchiectasis, asthma and rhinitis.

Still more particularly, the compounds of formula (I) may be used in the treatment of chronic obstructive pulmonary disease (COPD), asthma and rhinitis.

Even more particularly, the compounds of formula (I) may be used in the treatment of chronic obstructive pulmonary disease (COPD).

Even more particularly, the compounds of formula (I) may be used in the treatment of cystic fibrosis.

Even more particularly, the compounds of formula (I) may be used in the treatment of bronchiectasis.

It is to be understood that reference herein to chronic obstructive pulmonary disease (COPD) refers to all aspects of COPD including genetic COPD (α1-antitrypsin-deficiency)).

Thus, the present invention provides a compound of formula (I) as hereinbefore defined for use in therapy.

In a further aspect, the present invention provides the use of a compound of formula (I) as hereinbefore defined in the manufacture of a medicament for use in therapy.

In a further aspect, the present invention provides a compound of formula (I) as hereinbefore defined for use in the treatment of human diseases or conditions in which modulation of neutrophil elastase activity is beneficial.

In a further aspect, the present invention provides the use of a compound of formula (I) as hereinbefore defined in the manufacture of a medicament for the treatment of human diseases or conditions in which modulation of neutrophil elastase activity is beneficial.

In a further aspect, the present invention provides a compound of formula (I) as hereinbefore defined for use in the treatment of an inflammatory disease or condition.

In a further aspect, the present invention provides the use of a compound of formula (I) as hereinbefore defined in the manufacture of a medicament for use in the treatment of an inflammatory disease or condition.

In a further aspect, the present invention provides a compound of formula (I) as hereinbefore defined for use in treating adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis or gastric mucosal injury.

In a further aspect, the present invention provides the use of a compound of formula (I) or a pharmaceutically acceptable salt thereof as hereinbefore defined in the manufacture of a medicament for use in treating adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis or gastric mucosal injury.

In a further aspect, the present invention provides a compound of formula (I) as hereinbefore defined for use in treating chronic obstructive pulmonary disease (COPD).

In a further aspect, the present invention provides the use of a compound of formula (I) or a pharmaceutically acceptable salt thereof as hereinbefore defined in the manufacture of a medicament for use in treating chronic obstructive pulmonary disease (COPD).

The compound according to the invention may be particularly suitable for use in the treatment of COPD, including the treatment or prevention of symptoms of COPD. Such symptoms include one or more of, dyspnea (breathlessness or shortness of breath), decreased exercise capacity, chronic cough, wheezing or excessive sputum production.

Accordingly, in another aspect of the invention there is provided a compound of formula (I) as hereinbefore defined for use in the reduction of symptoms of COPD (including chronic bronchitis and emphysema).

In another aspect of the invention there is provided the use of a compound of formula (I) as hereinbefore defined in the manufacture of a medicament for use in the reduction of symptoms of COPD (including chronic bronchitis and emphysema).

Patients with COPD often experience exacerbations of the condition, resulting in an acute increase in disease symptoms. Such exacerbations are often caused by infection of the tracheobronchial tree or air pollution, however, in many patients the cause of exacerbations is unknown. Exacerbations are a poor prognostic factor for disease progression and patients with exacerbations often require hospitalisation. Exacerbations can result in a permanent reduction in lung function and a worsening of symptoms. There is therefore a need to find suitable methods for preventing or treating such exacerbations. A compound according to the present invention may be useful for the treatment of COPD exacerbations. For example, a compound according to the invention may be useful for treating the severity, frequency and/or duration of COPD exacerbations.

Accordingly, in another aspect of the invention there is provided a compound of formula (I) as hereinbefore defined for use in the reduction of severity, frequency and/or duration of exacerbations in a patient with COPD (including chronic bronchitis and emphysema).

According to another aspect of the invention there is provided the use of a compound of formula (I) as hereinbefore defined in the manufacture of a medicament for use in the reduction of severity, frequency and/or duration of exacerbations in a patient with COPD (including chronic bronchitis and emphysema).

A compound according to the invention may also be useful in stabilising or slowing down disease progression of COPD and may provide a disease modifying effect on COPD. Such disease modification may provide a sustained improvement in lung function and/or lung structure.

According to another aspect of the invention there is provided a compound of formula (I) as hereinbefore defined for use in stabilising or slowing down disease progression of COPD.

According to another aspect of the invention there is provided the use of a compound of formula (I) as hereinbefore defined in the manufacture of a medicament for use in stabilising or slowing down disease progression of COPD.

The compounds according to the invention may also be useful in treating patients with alpha-1-antitrypsin deficiency (AATD). AATD is a hereditary disease with known genotype and phenotype making it suitable for diagnostic screening and early intervention, for example by treatment before symptoms of the disease have developed. Patients with AATD are particularly prone to develop lung diseases such as COPD and emphysema.

Accordingly, there is provided a compound of formula (I) as hereinbefore defined for use in the treatment of AATD.

According to another aspect of the invention there is provided the use of a compound of formula (I) as hereinbefore defined in the manufacture of a medicament for use in the treatment of AATD.

In one embodiment there is provided a compound of formula (I) as hereinbefore defined for use in the treatment of a lung disease (for example COPD or emphysema) in a patient with AATD.

According to another aspect of the invention there is provided the use of a compound of formula (I) as hereinbefore defined in the manufacture of a medicament for use in the treatment of a lung disease (for example COPD or emphysema) in a patient with AATD.

Patients with AATD may be identified using known methods, for example as described in the minutes of the FDA Advisory Committee on Blood Products 95$^{th}$ Meeting, Jul. 20-21, 2009 and American Thoracic Society/ERS Statement: Standards for the Diagnosis and Management of Individuals with Alpha-1 Antitrypsin Deficiency, Am. J. Respir. Crit. Care Med. 2003; 168:820-899. Diagnosis could include, for example the detection of low serum levels of alpha-1 antitrypsin using conventional methods such as a suitable immunoassay. Currently a serum level below 11 μM (80 mg/dL) is considered to be indicative of AATD, although there is debate about the accuracy of a serum level to determine that a patient has AATD as serum levels can vary between patients. A more accurate method may be to use a genotype test to detect identify alpha-1-antitrypsin deficient alleles, particularly the PI*SZ and PI*ZZ alleles. Patients that are homozygous (PI*ZZ) are expected to be particularly prone to developing conditions such as emphysema or COPD. However heterozygous patients with the PI*Z allele may also be prone to such conditions. Alternatively a phenotype test could be used to determine the specific alpha-1-antitrypsin in a patient. Diagnostic testing could be carried out on a patient without symptoms of a disease. Accordingly, diagnostic testing could be used to identify a patient with AATD and then treat that patient with a compound according to the invention to prevent or delay the onset of conditions such as COPD or emphysema. Alternatively, testing for AATD may be carried out on a patient with symptoms of a disease or condition such as COPD or emphysema, and then treating the patient with a compound according to the invention if the patient has AATD.

In one embodiment there is provided a compound of formula (I) as hereinbefore defined for use in the treatment of a lung disease (for example COPD or emphysema) in a patient diagnosed with AATD. In this embodiment the patient may be diagnosed using, for example, one of the methods described hereinbefore.

Accordingly, a compound according to the present invention may be used as a preventative treatment in symptom free patients with AATD to provide disease modification by, for example, preventing the disease from progressing into an active disease state. Alternatively, in AATD patients with an active disease, a compound according to the present invention could be used as a treatment to modify disease progression, for example by slowing down the progression of COPD or emphysema in an AATD patient.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treating, or reducing the risk of, a disease or condition in which inhibition of neutrophil elastase activity is beneficial which comprises administering to a patient in need thereof a therapeutically effective amount of a compound of formula (I) as hereinbefore defined.

The invention still further provides a method of treating, or reducing the risk of, an inflammatory disease or condition which comprises administering to a patient in need thereof a therapeutically effective amount of a compound of formula (I) as hereinbefore defined.

The invention still further provides a method of treating, or reducing the risk of, adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractory asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn's disease, ulcerative colitis or gastric mucosal injury which comprises administering to a patient in need thereof a therapeutically effective amount of a compound of formula (I) as hereinbefore defined.

The invention still further provides a method of treating, or reducing the risk of, chronic obstructive pulmonary disease (COPD) which comprises administering to a patient in need thereof a therapeutically effective amount of a compound of formula (I) as hereinbefore defined.

The invention still further provides a method of treating, or reducing the risk of, cystic fibrosis, which comprises administering to a patient in need thereof a therapeutically effective amount of a compound of formula (I) as hereinbefore defined.

The invention still further provides a method of treating, or reducing the risk of, bronchiectasis, which comprises administering to a patient in need thereof a therapeutically effective amount of a compound of formula (I) as hereinbefore defined.

The invention still further provides a method of treating, or reducing the risk of, AATD, which comprises administering to a patient in need thereof a therapeutically effective amount of a compound of formula (I) as hereinbefore defined.

The invention still further provides a method of treating, or reducing the risk of, AATD, which comprises diagnosing a patient with AATD and administering to said patient a therapeutically effective amount of a compound of formula (I) as hereinbefore defined.

The invention still further provides a method of treating, or reducing the risk of, a lung disease such as COPD or emphysema in a patient with AATD, which comprises administering to a patient in need thereof a therapeutically effective amount of a compound of formula (I) as hereinbefore defined.

The invention still further provides a method of treating, or reducing the risk of, a lung disease such as COPD or emphysema in a patient with AATD, which comprises
  (i) testing a patient for AATD; and
  (ii) when said testing determines that said patient has AATD, administering a therapeutically effective amount of a compound of formula (I) as hereinbefore defined.

In this embodiment the patient in step (i) may be symptom-free of a lung disease before being tested for AATD. Alternatively the patient may have symptoms of a lung disease such as COPD or emphysema, prior to testing for AATD.

In this embodiment the testing/diagnosis of AATD may, for example be carried out as hereinbefore defined.

For the above-mentioned therapeutic uses the dosage administered will, of course, vary with the compound employed, the mode of administration, the treatment desired and the disorder indicated. The daily dosage of the compound of the invention may be in the range from 0.001 mg/kg to 100 mg/kg, for example 0.001 to 1 mg/kg, suitably 0.001 to 0.1 mg/kg.

The compounds of formula (I) may be used on their own but will generally be administered in the form of a pharmaceutical composition in which the formula (I) compound (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Another suitable pharmaceutical composition of this invention is one suitable for inhaled administration, inhalation being a particularly useful method for administering the compounds of the invention when treating respiratory diseases such as chronic obstructive pulmonary disease (COPD) or asthma. When administered by inhalation the compounds of formula (I) may be used effectively at doses in the µg/kg range, for example 0.1 to 500 µg/kg, 0.1 to 50 µg/kg, 0.1 to 40 µg/kg, 0.1 to 30 µg/kg, 0.1 to 20 µg/kg, 0.1 to 10 µg/kg, 5 to 10 µg/kg, 5 to 50 µg/kg, 5 to 40 µg/kg, 5 to 30 µg/kg, 5 to 20 µg/kg, 5 to 10 µg/kg, 10 to 50 µg/kg, 10 to 40 µg/kg 10 to 30 µg/kg, or 10 to 20 µg/kg of active ingredient. For example a dose of 1, 2, 4, 6, 8 or 10 µg/kg of active ingredient. The doses may be administered as a single daily dose or as multiple doses per day, for example twice daily dosing using one of the above mentioned doses for each administration, such as 0.1 to 30 µg/kg administered twice per day. Suitably, however the dose is administered as a single dose once per day.

In an embodiment of the invention, there is provided a pharmaceutical composition comprising a compound of the invention as hereinbefore defined, in association with a pharmaceutically acceptable adjuvant, diluent or carrier, which is formulated for inhaled administration.

When administered by inhalation, metered dose inhaler devices may be used to administer the active ingredient, dispersed in a suitable propellant and with or without additional excipients such as ethanol, surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients. Nebulised aqueous suspensions or, preferably, solutions may also be employed, with or without a suitable pH and/or tonicity adjustment, either as a unit-dose or multi-dose formulations. For example a suitable composition for inhalation comprises a compound of the formula (I) dissolved in an aqueous medium (mg/ml in Mill-Q water) comprising sodium chloride (8.5 mg/ml); citric acid dried (0.28 mg/ml); sodium citrate (0.5 mg/ml); and Polysorbate 80 (0.2 mg/ml).

Dry powder inhalers may be used to administer the active ingredient, alone or in combination with a pharmaceutically acceptable carrier, in the later case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

Dry powder inhalers may be used to administer the active ingredient, alone or in combination with a pharmaceutically acceptable carrier, in the later case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

In a further embodiment, the pharmaceutical composition is administered by means of a dry powder inhaler (DPI).

The DPI may be "passive" or breath-actuated, or "active" where the powder is dispersed by some mechanism other than the patient's inhalation, for instance, an internal supply of compressed air. At present, three types of passive dry powder inhalers are available: single-dose, multiple unit dose or multi-dose (reservoir) inhalers. In single-dose devices, individual doses are provided, usually in gelatine capsules, and have to be loaded into the inhaler before use, examples of which include Spinhaler® (Aventis), Rotahaler®(GlaxoSmithKline), Aeroliser™ (Novartis), Inhalator® (Boehringer) and Eclipse (Aventis) devices. Multiple unit dose inhalers contain a number of individually packaged doses, either as multiple gelatine capsules or in blisters, examples of which include Diskhaler® (GlaxoSmithKline), Diskus® (GlaxoSmithKline) and Aerohaler® (Boehringer) devices. In multi-dose devices, drug is stored in a bulk powder reservoir from which individual doses are metered, examples of which include Turbuhaler® (AstraZeneca), Easyhaler® (Orion), Novolizer® (ASTA Medica), Clickhaler® (Innovata Biomed) and Pulvmal (Chiesi) devices.

An inhalable pharmaceutical composition or dry powder formulation for use in a DPI can be prepared by mixing finely divided active ingredient (having a mass median diameter generally equal to or less than 10 µm, preferably equal to or less than 5 µm) with a carrier substance, for example, a mono-, di- or polysaccharide, a sugar alcohol, or another polyol. Suitable carriers are sugars or sugar alcohols, for example, lactose, glucose, raffinose, melezitose, lactitol, maltitol, trehalose, sucrose, mannitol; and starch. If required the dry powder composition may contain a suitable coating agent such as magnesium stearate, ascorbyl palmetate or sodium stearyl fumarate. Alternatively the Form of Compound (I) may be used alone in a DPI. The powder mixture (or Form of compound (I) alone) may then, as required, be dispensed into hard gelatine capsules or blisters, each containing the desired dose of the active ingredient.

Alternatively, an inhalable pharmaceutical composition may be prepared by processing a finely divided powder (e.g. consisting of finely divided active ingredient and finely divided carrier particles) into spheres that break up during the inhalation procedure. This spheronized powder is filled into the drug reservoir of a multidose inhaler, for example, that known as the Turbuhaler® in which a dosing unit meters the desired dose which is then inhaled by the patient.

In a further embodiment, the pharmaceutical composition is administered by means of a metered dose inhaler, particularly a pressurised metered dose inhaler (pMDI). The pMDI contains the active as a suitable solution or suspension in a pressurised container. The active is delivered by actuating a valve on the pMDI device. Actuation may be manual or breath actuated. In manually actuated pMDIs the device is actuated by for example pressing a suitable release mechanism on the pMDI device as the patient inhales. Breath actuated pMDIs are actuated when the patient inhales through the mouthpiece of the pMDI. This can be advantageous as the actuation of the device is timed with the patients' inhalation and can result in a more consistent dosing of the active. Examples of pMDI devices include for example Rapihaler® (AstraZeneca).

When administered intra-nasally, a compound of formula (I) as hereinbefore defined could be administered as a solution, or a suspension in a suitable aqueous medium for a suitable nasal delivery device such as a spray pump or a pMDI. Alternatively the compound could be administered as a dry powder composition as hereinbefore described using a suitable DPI device. If it is desirable to keep the compound in the nasal region it may be necessary to use a larger particle size in the dry powder composition, for example greater than 10 µm, such as 10 to 50 µm.

Accordingly, the present invention also provides an inhaler device (for example a dry powder inhaler, in particular a multiple unit dose dry powder inhaler, or a pMDI inhaler) containing an inhalable pharmaceutical composition of the invention.

The compounds of the invention may also be administered in conjunction with other compounds used for the treatment of the above conditions.

The invention further relates to combination therapies wherein a compound of the invention or a pharmaceutical composition or formulation comprising a compound of the invention, is administered concurrently or sequentially or as a combined preparation with another therapeutic agent or agents, for the treatment of one or more of the conditions listed.

The invention further relates to a combination product comprising of the formula (I) and another therapeutic agent, for use in the treatment of an inflammatory disease, wherein the compound of formula (I) and the other therapeutic agent are administered concurrently or sequentially or as a combined preparation.

In particular, the combination therapies and combination products may be used for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 23, and interleukin antagonists or inhibitors such as anakinra; tumour necrosis factor alpha (TNF-$\alpha$) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, with a monoclonal antibody targeting B-Lymphocytes (such as CD20 (rituximab), MRA-aILl6R and T-Lymphocytes, CTLA4-Ig, HuMax Il-15).

The present invention still further relates to the combination of a compound of the invention, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BILL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, and a proton pump inhibitor (such as omeprazole) or a gastroprotective histamine type 2 receptor antagonist.

The present invention further relates to the combination of a compound of the invention, and an antagonist of the histamine type 4 receptor.

The present invention still further relates to the combination of a compound of the invention, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine, telenzepine or tolterodine.

The present invention still further relates to the combination of a compound of the invention, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof, indacaterol, milveterol or carmoterol.

The present invention further relates to the combination of a compound of the invention, and a chromone, such as sodium cromoglycate or nedocromil sodium. The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, with an agent that modulates a nuclear hormone receptor such as PPARs.

The present invention still further relates to the combination of a compound of the invention, together with an immunoglobulin (Ig) or Ig preparation or an antagonist or antibody modulating Ig function such as anti-IgE (for example omalizumab).

The present invention further relates to the combination of a compound of the invention, and another systemic or topically-applied anti-inflammatory agent, such as thalidomide or a derivative thereof, a retinoid, dithranol or calcipotriol.

The present invention still further relates to the combination of a compound of the invention, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example gefitinib or imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$.- or $B_2$.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ) (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$. or $NK_3$. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2×7; or (xxvii) inhibitor of transcription factor activation such as NFkB, API, or STATS.

A compound of the invention, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In particular the compounds of the invention may be administered in conjunction with a second active ingredient which is selected from:

a) a PDE4 inhibitor including an inhibitor of the isoform PDE4D;
b) a β-adrenoceptor agonist such as metaproterenol, isoproterenol, isoprenaline, albuterol, salbutamol, formoterol, salmeterol, terbutaline, orciprenaline, bitolterol mesylate, pirbuterol, indacaterol or carmoterol;
c) a muscarinic receptor antagonist (for example a M1, M2 or M3 antagonist, such as a selective M3 antagonist) such as ipratropium bromide, tiotropiuin bromide, oxitropium bromide, pirenzepine, telenzepine or tolterodine;
d) a modulator of chemokine receptor function (such as a CCR1 or CCR8 receptor antagonist);
e) an inhibitor of kinase function;
f) a non-steroidal glucocorticoid receptor agonist;
g) a steroidal glucocorticoid receptor agonist; and
h) a protease inhibitor (such as a MMP12 or MMP9 inhibitor).

In the above other pharmaceutical composition, process, method, use and medicament manufacture features, the alternative and preferred embodiments of the compounds of the invention described herein also apply.

EXAMPLES

The invention will now be illustrated by the following Examples in which, unless stated otherwise:

(i) temperatures are given in degrees Celsius (° C.); operations were carried out at room or ambient temperature, that is, at a temperature in the range of 18-25° C. and under an atmosphere of an inert gas such as argon.

(ii) NMR spectra were recorded on a Varian Mercury-VX 300 MHz instrument or a Varian Inova 400 MHz instrument. The central peaks of chloroform-d (H 7.27 ppm), acetone (H 2.05 ppm), dichloromethane-d2 (H 5.32 ppm) or DMSO-$d_6$ (H 2.50 ppm) were used as internal references. Alternatively, NMR spectra were recorded on a Varian Inova Unity 500 MHz instrument. Proton-NMR experiments were acquired using dual suppression of residual solvent peak and $H_2O$.

(iii) The following method was used for LC/MS analysis:

Instrument Agilent 1100; Column Waters Symmetry 2.1×30 mm; Mass APCI; Flow rate 0.7 mL/min; Wavelength 254 nm; Solvent A: water+0.1% TFA; Solvent B: acetonitrile+0.1% TFA; Gradient 15-95%/B 2.7 min, 95% B 0.3 min.

(iv) The following method was used for HPLC analysis:

LC Method A: HPLC method A was performed with Agilent 1100 series machines on Kromasil© C18 5 μm 3.0×100 mm column. Aqueous phase was water/TFA (99.8/0.1) and organic phase was acetonitrile/TFA (99.92/0.08). Flow was 1 ml/min and gradient was set from 10 to 100% of organic phase during 20 minutes. Detection was carried out on 220, 254 and 280 nm.

LC Method B: HPLC method B was performed with Agilent 1100 series machines on XTerra® $RP_8$ 5 μm 3.0×100 mm column. Aqueous phase was 15 nM $NH_3$ in water and organic phase was acetonitrile. Flow was 1 ml/min or 0.6 ml/min when indicated and gradient was set from 10 to 100% of organic phase during 20 minutes. Detection was carried out on 220, 254 and 280 nm LC Method C: HPLC method C was performed on Acquity BEH RP18 30×4.6 mm, 1.7μ column. Mobile phase A was water; mobile phase B was acetonitrile; mobile phase C was 1.0% TFA in water. Injection Volume was 5 μL; Column temperature was 40° C.; Flow rate was 2.0 mL/min; diluent was acetonitrile.

Gradient:

| Time | Mobile Phase A | Mobile Phase B | Mobile Phase-C |
| --- | --- | --- | --- |
| 0.0 | 92 | 05 | 03 |
| 2.5 | 62 | 35 | 03 |
| 5.2 | 07 | 90 | 03 |
| 5.7 | 07 | 90 | 03 |
| 5.8 | 92 | 05 | 03 |

Run time was 6.2 minutes; post time was 2.3 min; and detection was at 235 nm.

(v) In general, the course of reactions was followed by TLC and reaction times are given for illustration only.

(vi) Yields are given for illustration only and are not necessarily those which can be obtained by diligent process development; preparations were repeated if more material was required.

(vii) Chemical symbols have their usual meanings; SI units and symbols are used.

(viii) Solvent ratios are given in volume: volume (v/v) terms.

(ix) Mass spectra (MS) (loop) were recorded on a Micromass Platform LC equipped with HP 1100 detector; unless otherwise stated the mass ion quoted is (MH+).

(x) X-ray Powder Diffraction patterns were collected on a PANalytical X'Pert PRO MPD theta-theta system, equipped with a focusing beam Johansson monochromator and an X'Celerator detector, using CuKα1 radiation (1.5406 Å, 45 kV, 40 mA). The diffraction pattern was collected between 2 and 40 °2θ in a continuous scan mode. The scan speed was 0.86°/min. with an increment of 0.016°. Samples were mounted on single silicon crystal wafer mounts.

(xi) Humidity Interaction (hygroscopicity determination): The gravimetric responses of test samples to changes in humidity were investigated using a TGA 5000 (TA Instruments) Gravimetrical Vapour Sorption (GVS). The relative humidity (RH) was raised in steps of 10% to 90% RH and lowered back to 0% RH in two cycles. Each level of RH was held until the equilibrium condition (sample weight change<0.005 wt % per 10 minutes) was reached. 3-5 mg of the test sample was placed in the cup and evaluated. The hygroscopicity was calculated as the relative change in weight of the sample between 0% RH at the start of the second cycle and 80% RH during the increase of humidity in the second cycle. A person skilled in the art will recognize that the hygroscopicity of a sample is dependent on other factors than the pure solid form itself; for example, the purity and the crystallinity of the sample will have some impact on the result.

(xii) Unless stated otherwise, starting materials were commercially available. All solvents and commercial reagents were of laboratory grade and were used as received.

Abbreviations

| | |
|---|---|
| APCI-MS: | Atmospheric Pressure Chemical Ionisation Mass Spectroscopy |
| DMF: | N,N-dimethylformamide |
| DMSO: | Dimethylsulfoxide |
| EtOAc: | Ethyl acetate |
| EtOH: | Ethanol |
| eq: | equivalents |
| h: | hours |
| HPLC: | High Performance Liquid Chromatography |
| IPC: | In Process Control |
| i-PrOH: | Isopropanol (propan-2-ol) |
| LCMS: | Liquid Column Chromatography/Mass Spectroscopy |
| MeOH: | Methanol |
| min: | minutes |
| NH$_4$Ac | Ammonium acetate |
| rt: | Retention time |
| TFA: | Trifluoroacetic acid |
| THF: | Tetrahydrofuran |
| vols.: | volumes |

Example 1

1-{2-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]ethyl}-1-methylpyrrolidinium acetate

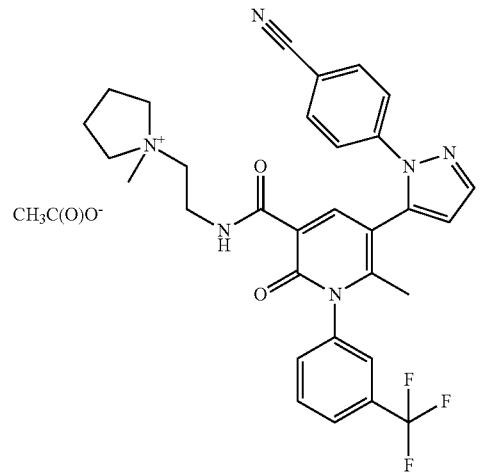 [SMILES: "CH3C(O)O-" ; Cc1c(-c2ccnn2-c2ccc(C#N)cc2)cc(C(=O)NCC[N+]2(C)CCCC2)c(=O)n1-c1cccc(C(F)(F)F)c1]

Step 1:

Ethyl 5-[1-(4-cyanophenyl)-1H-pyrazol-5-yl]-6-methyl-2-oxo-1-[3-(trifluoromethyl)phenyl]-1,2-dihydropyridine-3-carboxylate (Intermediate A) (200 mg, 0.41 mmol) and 2-pyrrolidin-1-ylethanamine (928 mg, 8.12 mmol, 20 eq) were dissolved in MeOH (2.5 mL) and heated to 100° C. in a sealed vial by a microwave oven for 40 min The solvent was evaporated and EtOH (3 mL) was added and heated to 50° C. for two hours and then water (3 mL) was added and the mixture was stirred at room temperature over night. The precipitate was centrifuged (4000 rpm, 3 min) and washed three times with EtOH/H$_2$O 1:1 (5 mL) and dried over night. The residue was dissolved in acetonitrile and purified by HPLC (30-95% MeOH in H$_2$O+0.1% TFA), the pure fractions were freeze-dried, dissolved in acetonitrile and desalted with Na$_2$CO$_3$ (solid phase) and evaporated to afford 5-[1-(4-cyanophenyl)-1H-pyrazol-5-yl]-6-methyl-2-oxo-N-(2-pyrrolidin-1-yl-ethyl)-1-[3-(trifluoromethyl)phenyl]-1,2-dihydropyridine-3-carboxamide as a white solid (156 mg, 65%); $^1$H NMR (500 MHz, DMSO): δ 1.67-1.59 (4H, m), 1.72 (3H, s), 2.43-2.37 (4H, m), 2.49-2.47 (2H, m), 3.38-3.33 (2H, m), 6.72 (1H, d), 7.67-7.63 (2H, m), 7.71 (1H, d), 7.88-7.82 (2H, m), 7.96-7.89 (4H, m), 8.07 (1H, s), 9.35 (1H, t);

APCI-MS$^m$/z: 561[MH$^+$]

Step 2:

5-[1-(4-cyanophenyl)-1H-pyrazol-5-yl]-6-methyl-2-oxo-N-(2-pyrrolidin-1-ylethyl)-1-[3-(trifluoromethyl)phenyl]-1,2-dihydropyridine-3-carboxamide (156 mg, 0.28 mmol) was dissolved in acetonitrile (4 mL), iodomethane (0.346 mL, 5.57 mmol, 20 eq) was added and heated to 55° C. over night. The solvent was evaporated and i-PrOH (4 mL) was added and heated to 50° C., the solvent was evaporated and to the residue of EtOH (2 mL) was added and heated to 50° C. and then i-PrOH (4 ml) of was added and the heater was turned off and stirred overnight. The solvents were evaporated and the residue was dissolved in acetonitrile and purified by HPLC using a gradient from 30% to 95% MeOH in H$_2$O (25 mM NH$_4$Ac, pH=5.2) for 20 min and at 95% for 10 min. The pure fractions were freeze-dried to obtain the title compound as white powder (65 mg, 37%); $^1$H NMR (500 MHz, DMSO) δ 1.73 (3H, s), 1.83 (3H, s), 2.09-2.01 (4H, m), 3.02 (3H, s), 3.53-3.40 (6H, m), 3.68 (2H, q), 6.72 (1H, d), 7.69-7.65 (2H, m), 7.73 (1H, d), 7.86 (1H, t), 7.89 (1H, s), 7.96-7.91 (4H, m), 8.03 (1H, s), 9.56 (1H, t); APCI-MS$^m$/z: 575[M$^+$]

LC (method A) rt=10.5 min

LC (method B) rt=13.0 min

Example 2

1-{-4-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]butyl}-1-methylpyrrolidinium acetate

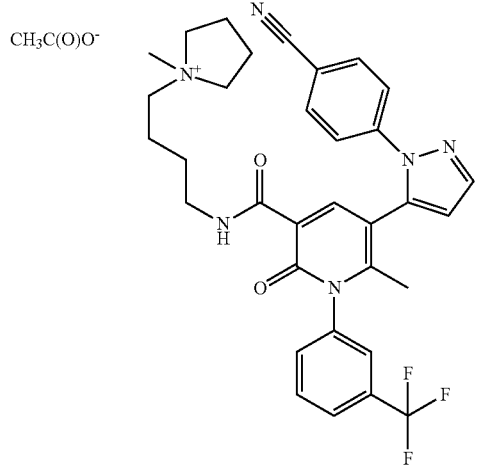 [SMILES: "CH3C(O)O-" ; Cc1c(-c2ccnn2-c2ccc(C#N)cc2)cc(C(=O)NCCCC[N+]2(C)CCCC2)c(=O)n1-c1cccc(C(F)(F)F)c1]

Example 3

2-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]-N,N,N-trimethylethanaminium acetate

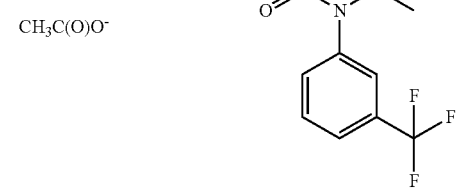

Step 1:

Intermediate A and 4-pyrrolidin-1-ylbutan-1-amine were reacted together using an analogous method to that described in Step 1 of Example 1 to afford 5-[1-(4-cyanophenyl)-1H-pyrazol-5-yl]-6-methyl-2-oxo-N-(4-pyrrolidin-1-ylbutyl)-1-[3-(trifluoromethyl)phenyl]-1,2-dihydropyridine-3-carboxamide as a white solid (169 mg, 67%); $^1$H NMR (500 MHz, DMSO) δ 1.50-1.36 (4H, m), 1.63 (4H, dd), 1.73 (3H, s), 2.40-2.30 (6H, m), 3.24 (2H, q), 6.72 (1H, d), 7.65 (2H, d), 7.71 (1H, d), 7.87-7.81 (2H, m), 7.95-7.89 (4H, m), 8.06 (1H, s), 9.30 (1H, t); APCI-MS$^m$/z: 589[MH$^+$]

Step 2:

5-[1-(4-cyanophenyl)-1H-pyrazol-5-yl]-6-methyl-2-oxo-N-(4-pyrolidin-1-ylbutyl)-1-[3-(trifluoromethyl)phenyl]-1,2-dihydropyridine-3-carboxamide was reacted with iodomethane using an analogous method to that described in Step 2 of Example 1 to afford the title compound (79 mg, 42%) as a white solid; $^1$H NMR (500 MHz, DMSO) δ 1.53-1.45 (2H, m), 1.65 (3H, s), 1.72-1.66 (2H, m), 1.79 (3H, s), 2.09-2.01 (4H, m), 2.95 (3H, s), 3.34-3.25 (4H, m), 3.49-3.35 (4H, m), 6.72 (1H, d), 7.68-7.65 (2H, m), 7.72 (1H, d), 7.89-7.83 (2H, m), 7.96-7.91 (4H, m), 8.04 (1H, s), 9.36 (1H, t); APCI-MS$^m$/z: 603[M$^+$]

LC (method A) rt=10.6 min

LC (method B) rt=13.1 min

Step 1:

Intermediate A and N,N-dimethylethane-1,2-diamine were reacted together using an analogous method to that described in Step 1 of Example 1 to afford 5-[1-(4-cyanophenyl)-1H-pyrazol-5-yl]-N-[2-(dimethylamino)ethyl]-6-methyl-2-oxo-1-[3-(trifluoromethyl)phenyl]-1,2-dihydropyridine-3-carboxamide (154 mg, 67%); $^1$H NMR (500 MHz, DMSO) δ 1.72 (3H, s), 2.10 (6H, s), 2.32 (2H, t), 3.36-3.32 (2H, m), 6.72 (1H, d), 7.67-7.64 (2H, m), 7.71 (1H, d), 7.88-7.82 (2H, m), 7.96-7.90 (4H, m), 8.07 (1H, s), 9.37 (1H, t); APCI-MS$^m$/z: 535[MH$^+$H]

Step 2.

5-[1-(4-cyanophenyl)-1H-pyrazol-5-yl]-N-[2-(dimethylamino)ethyl]-6-methyl-2-oxo-1-[3-(trifluoromethyl)phenyl]-1,2-dihydropyridine-3-carboxamide was reacted with iodomethane using an analogous method to that described in Step 2 of Example 1 to afford the title compound (109 mg, 62%) as a white solid; $^1$H NMR (500 MHz, DMSO) δ 1.63 (3H, s), 1.82 (3H, s), 3.08 (9H, s), 3.44 (2H, t), 3.68 (2H, q), 6.72 (1H, d), 7.67 (2H, d), 7.73 (1H, d), 7.85 (1H, t), 7.89 (1H, s), 7.97-7.91 (4H, m), 8.03 (1H, s), 9.56 (1H, t); APCI-MS$^m$/z: 549[M]

LC (method A) rt=10.1 min

LC (method B) rt=12.1 min

Example 4

4-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]-N,N,N-trimethylbutan-1-aminium iodide

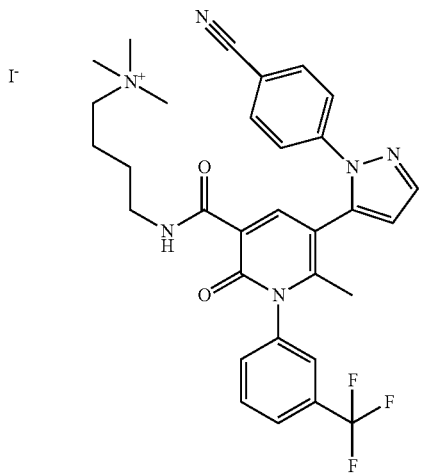 [SMILES: [I-] ; Cc1c(-c2ccnn2-c2ccc(C#N)cc2)cc(C(=O)NCCCC[N+](C)(C)C)c(=O)n1-c1cccc(C(F)(F)F)c1]

Step 1:

Intermediate A and N,N-dimethylbutane-1,4-diamine were reacted together using an analogous method to that described in Step 1 of Example 1 to afford 5-[1-(4-cyanophenyl)-1H-pyrazol-5-yl]-N-[4-(dimethylamino)butyl]-6-methyl-2-oxo-1-[3-(trifluoromethyl)phenyl]-1,2-dihydropyridine-3-carboxamide (139 mg, 58%) as a white solid; $^1$H NMR (500 MHz, DMSO) δ 1.40 (4H, dq), 1.74 (3H, s), 2.06 (6H, s), 2.15 (2H, t), 3.24 (2H, q), 6.72 (1H, d), 7.67-7.64 (2H, m), 7.71 (1H, d), 7.88-7.81 (2H, m), 7.95-7.89 (4H, m), 8.06 (1H, s), 9.30 (1H, t); APCI-MS$^m$/z: 563[MH$^+$]

Step 2:

5-[1-(4-cyanophenyl)-1H-pyrazol-5-yl]-N-[4-(dimethylamino)butyl]-6-methyl-2-oxo-1-[3-(trifluoromethyl)phenyl]-1,2-dihydropyridine-3-carboxamide (139 mg, 0.25 mmol) was dissolved in acetonitrile (4 mL), iodomethane (0.308 mL, 4.94 mmol, 20 eq) was added and heated to 55° C. over night. The solvent was evaporated, i-PrOH (4 mL) was added, heated to 50° C., the solvent was evaporated and to the residue was EtOH (2 mL) added and heated to 50° C. and then i-PrOH (4 mL) was added and the heater was turned off and stirred over night.

The formed precipitate was filtered off, washed with i-PrOH and dried to give the title compound as a white solid (54 mg, 31% yield); $^1$H NMR (500 MHz, DMSO) δ 1.47 (2H, quintet), 1.70-1.61 (2H, m), 1.79 (3H, s), 3.00 (9H, s), 3.30-3.25 (4H, m), 6.72 (1H, d), 7.67 (2H, d), 7.71 (1H, d), 7.89-7.82 (2H, m), 7.96-7.91 (4H, m), 8.04 (1H, s), 9.35 (1H, t); APCI-MS$^m$/z: 577[M$^+$]

LC (method A) rt=10.2 min
LC (method B) rt=13.1 min

Example 5

1-{3-[({5-[1-(4-cyanophenyl)-1H-pyrazol-5-yl]-6-methyl-2-oxo-1-[3-(trifluoromethyl)phenyl]-1,2-dihydropyridin-3-yl}carbonyl)amino]propyl}-1-methylpyrrolidinium iodide

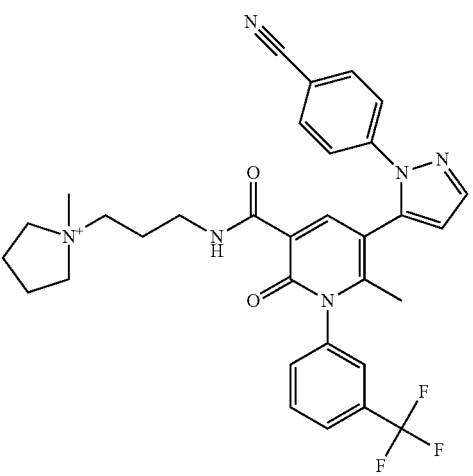

Step 1:

Intermediate A and 3-pyrrolidin-1-ylpropan-1-amine were reacted together using an analogous method to that described in Step 1 of Example 1 to afford 5-[1-(4-cyanophenyl)-1H-pyrazol-5-yl]-6-methyl-2-oxo-N-N-(3-pyrrolidin-1-ylpropyl)-1-[3-(trifluoromethyl)phenyl]-1,2-dihydropyridine-3-carboxamide (182 mg, 74%) as a white solid; $^1$H NMR (500 MHz, DMSO) δ 1.65-1.56 (6H, m), 1.73 (3H, s), 2.39-2.32 (6H, m), 3.30-3.24 (2H, m), 6.72 (1H, d), 7.67-7.64 (2H, m), 7.71 (1H, d), 7.87-7.81 (2H, m), 7.95-7.89 (4H, m), 8.06 (1H, s), 9.36 (1H, t); APCI-MS$^m$/z: 575[MH$^+$]

Step 2:

5-[1-(4-cyanophenyl)-1H-pyrazol-5-yl]-6-methyl-2-oxo-N-(3-pyrrolidin-1-ylpropyl)-1-[3-(trifluoromethyl)phenyl]-1,2-dihydropyridine-3-carboxamide was reacted with iodomethane using an analogous method to that described in Step 2 of Example 4 to afford the title compound (154 mg, 68%) as a white solid; $^1$H NMR (500 MHz, DMSO) δ 1.82 (3H, s), 1.93 (2H, td), 2.10-2.01 (4H, m), 2.94 (3H, s), 3.31-3.27 (4H, m), 3.49-3.34 (4H, m), 6.72 (1H, d), 7.67 (2H, d), 7.71 (1H, d), 7.88-7.83 (2H, m), 7.97-7.91 (4H, m), 8.03 (1H, s), 9.40 (1H, t); APCI-MS$^m$/z: 589[M$^+$]

LC (method A) rt=10.4 min
LC (method B) rt=13.1 min

Example 6

3-[({6-[1-(4-cyanophenyl)-1H-pyrazol-5-yl]-5-methyl-3-oxo-4-[3-(trifluoromethyl)phenyl]-3,4-dihydropyrazin-2-yl}carbonyl)amino]-N,N,N-trimethylpropan-1-aminium iodide

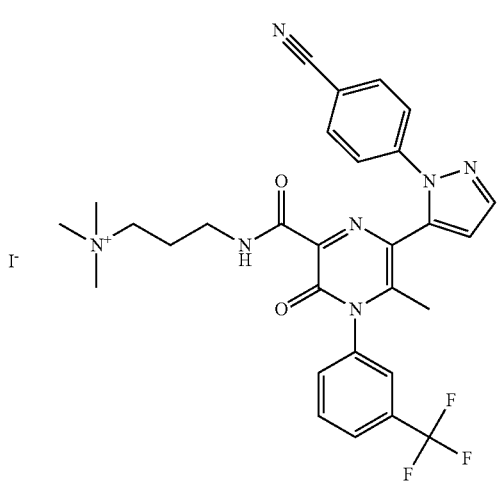 [SMILES: [I-] ; Cc1c(-c2ccnn2-c2ccc(C#N)cc2)nc(C(=O)NCCC[N+](C)(C)C)c(=O)n1-c1cccc(C(F)(F)F)c1]

Step 1:

Methyl 6-[1-(4-cyanophenyl)-1H-pyrazol-5-yl]-5-methyl-3-oxo-4-[3-(trifluoromethyl)phenyl]-3,4-dihydropyrazine-2-carboxylate (synthesised according to WO2009/061271, Example 1 intermediate) and N,N-dimethylpropane-1,3-diamine were reacted together using an analogous method to that described in Step 1 of Example 1 to afford 6-[1-(4-cyanophenyl)-1H-pyrazol-5-yl]-N-[3-(dimethylamino)propyl]-5-methyl-3-oxo-4-[3-(trifluoromethyl)phenyl]-3,4-dihydropyrazine-2-carboxamide (54 mg, 19%) as a white solid; APCI-MS$^m$/z: 550 [MH$^+$].

Step 2:

6-[1-(4-Cyanophenyl)-1H-pyrazol-5-yl]-N-[3-(dimethylamino)propyl]-5-methyl-3-oxo-4-[3-(trifluoromethyl)phenyl]-3,4-dihydropyrazine-2-carboxamide was reacted with iodomethane using an analogous method to that described in Step 2 of Example 4 to afford the title compound (26 mg, 24%) as a white solid; $^1$H NMR (500 MHz, DMSO) δ 1.91-1.83 (2H, m), 1.93 (3H, s), 3.01 (9H, s), 3.30-3.23 (4H, m), 6.77 (1H, d), 7.69 (2H, d), 7.78 (1H, d), 7.92-7.87 (3H, m), 7.99-7.93 (3H, m), 8.93 (1H, t); APCI-MS$^m$/z: 564 [M$^+$]

LC (method A) rt=9.5 min

LC (method B) rt=11.3 min

Example 7

3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium bromide

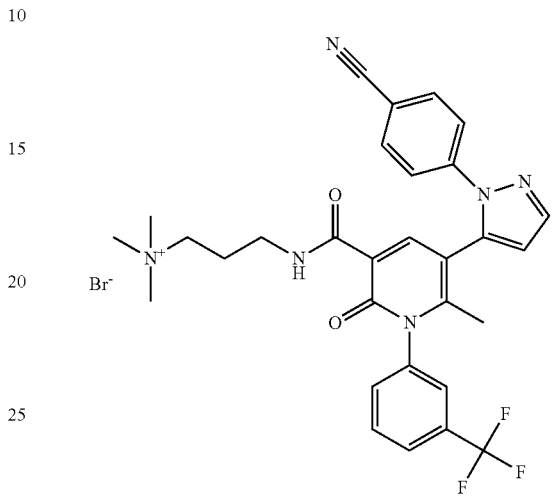

Step 1:

A suspension of ethyl 5-(1-(4-cyanophenyl)-1H-pyrazol-5-yl)-6-methyl-2-oxo-1-(3-(trifluoromethyl)phenyl)-1,2-dihydropyridine-3-carboxylate (Intermediate A) (9.85 g, 20.00 mmol), N,N-dimethylpropane-1,3-diamine (37.8 mL, 300.03 mmol) in EtOH (150 mL) in a 500 mL round-bottomed flask was heated to reflux. Within 30 minutes a clear solution was obtained. After 6 hours the heating was turned off.

After cooling to room temperature the solvents were evaporated and the orange colored crystalline residue was recrystallized from 150 mL of ethanol. The crude product was washed with small amounts of ethanol and dried to afford 5-(1-(4-cyanophenyl)-1H-pyrazol-5-yl)-N-(3-(dimethylamino)propyl)-6-methyl-2-oxo-1-(3-(trifluoromethyl)phenyl)-1,2-dihydropyridine-3-carboxamide (10 g, 91%) as a white solid; $^1$H NMR (400 MHz, DMSO) δ 9.31 (1H, t), 8.07 (1H, s), 7.93 (4H, m), 7.86 (1H, s), 7.84 (1H, t), 7.71 (1H, d), 7.66 (2H, d), 6.72 (1H, d), 3.25 (2H, q), 2.17 (2H, t), 2.07 (6H, s), 1.73 (3H, s), 1.56 (2H, m).

Step 2:

In a stainless-steel high-pressure reactor (Parr) were placed 5-(1-(4-cyanophenyl)-1H-pyrazol-5-yl)-N-(3-(dimethylamino)propyl)-6-methyl-2-oxo-1-(3-(trifluoromethyl)phenyl)-1,2-dihydropyridine-3-carboxamide (14.7 g, 26.80 mmol) and acetonitrile (200 mL) and the vessel cooled with dry ice (CO$_2$).

Via a Teflon tubing bromomethane (density 1.9 g/mL at −30° C.) (24.21 mL, 484.52 mmol) was condensed into a cylinder cooled with dry ice ethanol (−78° C.). The condensed bromomethane was poured into the mixture in the Parr, which was sealed and heated to 70° C. under vigorous stirring overnight. (The pressure obtained was below 1 bar).

After 18 hours the reactor was cooled, opened and the solvents were removed by reduced pressure. The residue was dissolved in a mixture of 2-propanol:ethanol (5:1) (80 mL) and heated to 80° C. for 1 hr and then stirred at room temperature for 4 h. The formed precipitate was filtered off and washed once with a mixture of 2-propanol:ethanol (5:1) 30 mL, three times with heptane (3×20 mL) and air dried to afford 14.9 g of a white powder. Ethanol 80 mL was added to this solid and the suspension was heated to reflux and was then stirred at room temperature over night. The formed precipitate was filtered off and washed with small amounts of ethanol and dried at 50° C. in vacuum to afford the title compound (10.7 g, 62%) as a white solid; $^1$H NMR (400 MHz, dmso) δ 1.81 (3H, s), 1.90 (2H, m), *(2H in solvent peak), 3.01 (9H, s), 3.26 (2H, m), 6.72 (1H, d), 7.67 (2H, d), 7.71 (1H, d), 7.86 (2H, m), 7.94 (4H, m), 8.04 (1H, s), 9.41 (1H, t); APCI-MS$^m$/z: 563 [M$^+$]

LC (method A) rt=8.6 min
LC (method B) rt=11.8 min

Example 8

3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium acetate 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium bromide (4.20 g, 6.53 mmol) (the product from Example 7, Step 2) was converted to the acetate salt by ion exchange performed on prep HPLC with CH$_3$CN:25 mM NH$_4$Ac as eluent to give the title product as a light yellow solid (3.31 g, 81%). $^1$H NMR (400 MHz, dmso) δ 1.67 (3H, s), 1.81 (3H, s), 1.85-1.94 (2H, m), 3.01 (9H, s), 3.23-3.33 (4H, m), 6.72 (1H, d), 7.67 (2H, d), 7.70 (1H, d), 7.83-7.88 (2H, m), 7.91-7.97 (4H, m), 8.04 (1H, s), 9.41 (1H, t); APCI-MS$^m$/z: 563 [M$^+$]

Example 9

3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate (Form A)

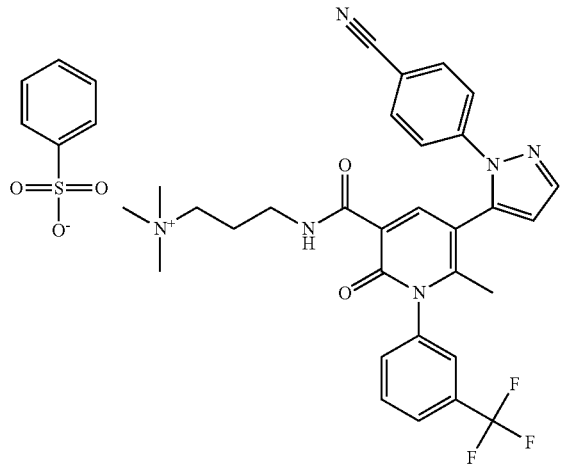 [SMILES: O=S(=O)([O-])c1ccccc1 ; Cc1c(-c2ccnn2-c2ccc(C#N)cc2)cc(C(=O)NCCC[N+](C)(C)C)c(=O)n1-c1cccc(C(F)(F)F)c1]

A column of DOWEX 1×8 (50-100 mesh, Cl$^-$) (approximately 10 g) was activated by passing through a aqueous saturated NaHCO$_3$-solution (approximately 70 mL), followed by washing with H$_2$O (100 mL) (until the pH of the eluent was neutral) and MeOH (40 mL). 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium acetate (300 mg, 0.48 mmol, Example 8) was dissolved in MeOH (2 mL) and the solution was allowed to pass slowly through the column followed by about 20 mL of MeOH. Benzenesulfonic acid (76 mg, 0.48 mmol) was added to the filtrate and the solution was evaporated, the residue was co-evaporated with EtOH and then dissolved in EtOH (0.5 mL) and THF (3.5 mL). The mixture was heated at 50° C. for 0.5 hr and was then stirred at room temperature over the weekend. No precipitate had formed over this time. Diethylether (3 mL) was added and the mixture was stirred at room temperature. After 1 hr a solid had started to precipitate and the slurry was stirred overnight. The precipitate was filtered off, washed with heptane and dried to afford the title compound as an off-white solid (300 mg, 86%); $^1$H NMR (400 MHz, dmso) δ 1.81 (3H, s), 1.90 (2H, m), 3.01 (9H, s), 3.27 (4H, m), 6.72 (1H, d), 7.30 (3H, m), 7.59 (2H, m), 7.67 (2H, d), 7.71 (1H, d), 7.85 (2H, m), 7.94 (4H, m), 8.04 (1H, s), 9.41 (1H, t). APCI-MS$^m$/z: 563 [M$^+$]

LC (method A) rt=9.9 min
LC (method B) rt=12.6 min

XRPD

XRPD analysis of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form A showed than the material was crystalline with an XRPD substantially as shown in FIG. 1. The most prominent peaks (2θ value) of Form A are shown in Table 1 in the description above.

Hygroscopicity

The hygroscopicity of the Form A, measured as described in (xi) above, was 0.8% (w/w).

Example 9a 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate (Form A)

A solution of 5-(1-(4-cyanophenyl)-1H-pyrazol-5-yl)-N-(3-(dimethylamino)propyl)-6-methyl-2-oxo-1-(3-(trifluoromethyl)phenyl)-1,2-dihydropyridine-3-carboxamide (synthesised according to Example 7, step 1) (14.40 g, 26.25 mmol) and methyl benzenesulfonate (3.82 ml, 28.88 mmol) in acetone (127 ml) was heated at 55° C. for 18 h. The solvents were removed by rotary evaporation and the foam-like residue was suspended in a mixture of 2-propanol:ethanol (5:1) (100 mL) and heated to 80° C. and was then stirred at room temperature over night. The precipitate was filtered off, washed twice with a mixture of 2-propanol:ethanol (5:1) (2×20 mL), washed once with heptane (50 mL) and air dried to afford 16.94 g of a white powder. The solid was further dried at 55° C. in vacuum overnight to afford of the title compound (16.75 g, 88%) as an off-white solid; $^1$H NMR (400 MHz, dmso) δ 1.81 (3H, s), 1.90 (2H, m), 3.01 (9H, s), 3.27 (4H, m), 6.72 (1H, d), 7.30 (3H, m), 7.59 (2H, m), 7.67 (2H, d), 7.71 (1H, d), 7.85 (2H, m), 7.94 (4H, m), 8.04 (1H, s), 9.41 (1H, t); APCI-MS m/z: 563 [M$^+$].

LC (method A) rt=9.9 min
LC (method B) rt=12.6 min

Example 10

3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate (Form B)

Batch 1

Methyl benzenesulfonate (13.0 ml, 0.099 mol, 1.1 equiv.) was charged to a solution of 5-(1-(4-cyanophenyl)-1H-pyrazol-5-yl)-N-(3-(dimethylamino)propyl)-6-methyl-2-oxo-1-(3-(trifluoromethyl)phenyl)-1,2-dihydropyridine-3-carboxamide (prepared using the method described in Example 7, step 1) (49.4 g, 90.0 mmol, 1.0 eq.) in acetone (0.434 L, 8.8 vols) at ambient temperature. The solution was heated to 55° C. and stirred for 1 h. An IPC by $^1$H NMR showed the reaction to be complete and the mixture was cooled to ambient. After stirring at ambient temperature overnight a white solid had formed. The solid was collected by filtration, the cake was washed with cold acetone (2×100 ml, 2×2 vols) and heptane (100 ml, 2 vols), and dried under suction until no further liquid was lost from the cake. The damp solid was transferred to a powder flask and dried to constant weight on a rotary at 40° C. to afford 46.5 g (72% Th.) of the title compound; $^1$H NMR (400 MHz, dmso) δ 1.81 (3H, s), 1.90 (2H, m), 3.01 (9H, s), 3.27 (4H, m), 6.72 (1H, d), 7.30 (3H, m), 7.59 (2H, m), 7.67 (2H, d), 7.71 (1H, d), 7.85 (2H, m), 7.94 (4H, m), 8.04 (1H, s), 9.41 (1H, t).

HPLC: 99.53% a/a, NSI>1%

Batch 2

Methyl benzenesulfonate (63.1 ml, 0.48 mol, 1.1 equiv.) was charged over 5 min to a solution of 5-(1-(4-cyanophenyl)-1H-pyrazol-5-yl)-N-(3-(dimethylamino)propyl)-6-methyl-2-oxo-1-(3-(trifluoromethyl)phenyl)-1,2-dihydropyridine-3-carboxamide (prepared using the method described in Example 7, step 1) (238 g, 0.433 mol, 1.0 equiv.) in acetone (2.09 L, 8.8 vols) at 30° C. The solution was heated to 55° C. and stirred for 2 h 20 min. An IPC by $^1$H NMR showed <3% starting material. The reaction mixture was cooled to 15° C. and stirred over night. No product precipitated during this time. The solvent was removed on a rotary evaporator at 35° C. to afford the crude product as a foam (368 g). The crude material was combined with the 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate of Batch 1 above (46.5 g). The crude material was slurried in 5:1 2-propanol/ethanol (1.97 L) for 1 h at reflux, the suspension was cooled and the solid was collected by filtration. The form of the solid appeared to have been altered since the material was no longer soluble in the 2-propanol/ethanol mix and the particle size appeared bigger. The filter cake was washed with 5:1 2-propanol/ethanol (2×400 ml) and heptane (1×900 ml) then dried under suction until no more solvent was pulled through. The damp solid was dried to constant weight in a vacuum oven to afford the title product (310 g); $^1$H NMR (400 MHz, dmso) δ 1.81 (3H, s), 1.90 (2H, m), 3.01 (9H, s), 3.27 (4H, m), 6.72 (1H, d), 7.30 (3H, m), 7.59 (2H, m), 7.67 (2H, d), 7.71 (1H, d), 7.85 (2H, m), 7.94 (4H, m), 8.04 (1H, s), 9.41 (1H, t).

Quantitative $^1$H NMR gave a strength of 97.3% w/w

XRPD

An X-ray powder diffractometry measurement on the isolated Batch 2 of 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form B showed that the solid was a different crystalline form compared to Form A described in Examples 9 and 9a. Form B is crystalline with an XRPD substantially as shown in FIG. 2. The most prominent peaks (2θ value) of Form B are shown in Table 2 in the description above.

Hygroscopicity

The hygroscopicity of the Form B, measured as described in (xi) above, was 0.4% (w/w).

Example 11

3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzene sulfonate (Form B)

A solution of 5-(1-(4-cyanophenyl)-1H-pyrazol-5-yl)-N-(3-(dimethylamino)propyl)-6-methyl-2-oxo-1-(3-(trifluoromethyl)phenyl)-1,2-dihydropyridine-3-carboxamide (5 g, 9.12 mmol) and methyl benzenesulfonate (1.67 g, 9.52 mmol) in acetone (50 mL) was heated at 55° C. for 4 h. After cooling the reaction mixture to room temperature, 2-methyltetrahydrofuran (50 mL) was added. The resulting mixture was stirred overnight. The precipitate was filtered and dried in vacuum oven to give the title product as a light brown solid (6 g, 90%); $^1$H NMR (400 MHz, DMSO-$d_6$) δ 9.35 (t, 1 H), 7.97 (s, 1 H), 7.83-7.94 (m, 4 H), 7.73-7.83 (m, 2 H), 7.64 (d, 1 H), 7.60 (d, 2 H), 7.46-7.56 (m, 2 H), 7.15-7.31 (m, 3 H), 6.65 (d, 1 H), 3.14-3.24 (m, 4 H), 2.94 (s, 9 H), 1.78-1.90 (m, 2 H), 1.75 (s, 3 H).

The 5-(1-(4-cyanophenyl)-1H-pyrazol-5-yl)-N-(3-(dimethylamino)propyl)-6-methyl-2-oxo-1-(3-(trifluoromethyl)phenyl)-1,2-dihydropyridine-3-carboxamide used as the starting material was prepared as follows:

Methyl 3-oxo-3-(3-(trifluoromethyl)phenylamino)propanoate

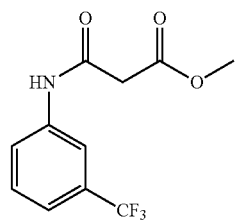 [SMILES: COC(=O)CC(=O)Nc1cccc(C(F)(F)F)c1]

Sodium hydrogen carbonate (36.3 kg, 1.7 mol eq) was charged followed by iso-propylacetate (102.5 L, 2.5 rel vol). 3-(trifluoromethyl)aniline (41.0 kg, 1 mol eq, limiting reagent) charged followed by a line rinse of iso-propylacetate (20.5 L, 0.5 rel vol). The reaction was cooled to 5° C.-10° C. Methyl malonyl chloride (36.5 kg, 1.05 mol eq) was charged maintaining the temperature below 10° C. followed by a line rinse of iso-propylacetate (10.3 L, 0.25 rel vol). The mixture was stirred until the reaction was complete as judged by HPLC. The temperature was adjusted to 20° C. and further iso-propylacetate (71.8 L, 1.75 rel vol) charged followed by water (205 L, 5 rel vol). The layers were separated & the organic layer further extracted with brine (41 L, 1 rel vol). The solvent was swapped from iso-propylacetate to cyclohexane by reduced pressure distillation. Following seeding, cooling to 5° C. and stirring, the product was isolated by filtration, washed twice with cyclohexane (2×41 L, 2×1 rel vol) and dried to constant weight to yield the title compound (60.6 kg, 232.2 mol, 91%).

6-Methyl-2-oxo-1-[3-(trifluoromethyl)phenyl]-1,2-dihydropyridine-3-carboxylic acid

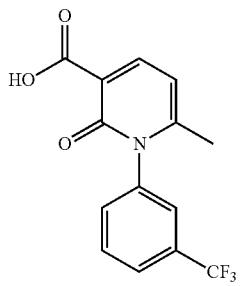 [SMILES: Cc1ccc(C(=O)O)c(=O)n1-c1cccc(C(F)(F)F)c1]

Methyl 3-oxo-3-(3-(trifluoromethyl)phenylamino)propanoate (62.0 kg, 1 mol eq, limiting reagent) was charged followed by ethanol (310 L, 5 rel vol, 5.3 rel vol). 4,4-dimethoxybutan-2-one (37.6 kg, 1.2 mol eq) was charged followed by an ethanol line rinse (18.6 L, 0.3 rel vol) and the temperature adjusted to 50° C. Sodium methoxide (30% w/w in methanol) (141.0 kg, 3.3 mol eq) charged maintaining the temperature below 55° C. An ethanol line rinse (31.0 L, 0.5 rel vol) was applied. The reaction was stirred until complete as judged by HPLC. Water (105.4 L, 1.7 rel vol) and 29% aqueous sodium hydroxide solution (17.2 kg, 0.52 mol eq) were charged. The reaction was stirred for 60 minutes. Hydrochloric acid (30% w/w) was charged until pH 2 achieved and was then cooled. The product was isolated by filtration, washed five times with water (5×124 L, 5×2 rel vol) and dried under vacuum to constant weight yielding the title compound (50.9 kg, 171.4 mol, 73.5%).

5-Iodo-6-methyl-2-oxo-1-[3-(trifluoromethyl)phenyl]-1,2-dihydropyridine-3-carboxylic acid

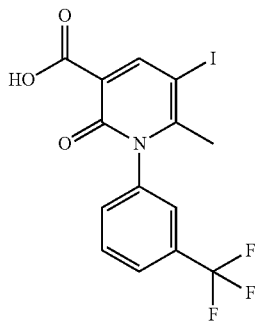 [SMILES: Cc1c(I)cc(C(=O)O)c(=O)n1-c1cccc(C(F)(F)F)c1]

To acetic acid (263.7 L, 6.8 rel vol) was charged 6-methyl-2-oxo-1-[3-(trifluoromethyl)phenyl]-1,2-dihydropyridine-3-carboxylic acid (38.6 kg, 1 mol eq, limiting reagent), iodine (17.4 kg, 0.53 mol eq) and concentrated sulfuric acid (3.7 L, 0.1 rel vol). The temperature was adjusted to 50° C.-55° C. and 90% nitric acid (4.1 kg, 0.6 mol eq) charged over 15 minutes. The reaction was stirred until deemed to be complete as judged by HPLC analysis. The reaction was cooled, stirred and the product collected by filtration. The solid was washed twice with water (2×77.0 L, 2×2 rel vol) and acetone (2×38.6 kg, 2×1 rel vol). The solid was dried under vacuum to constant weight to yield the title compound (47.0 kg, 111.0 mol, 85.7%).

N-[3-(dimethylamino)propyl]-5-iodo-6-methyl-2-oxo-1-[3-(trifluoromethyl)phenyl]-1,2-dihydropyridine-3-carboxamide

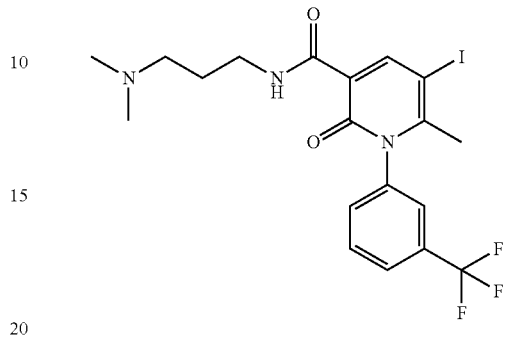

To a suspension of 5-iodo-6-methyl-2-oxo-1-[3-(trifluoromethyl)phenyl]-1,2-dihydropyridine-3-carboxylic acid (10 g, 23.64 mmol) in DMF (20 mL) was added a solution of carbonyldiimidazole (5.14 g, 30.72 mmol) in DMF (30 mL) over a period of 40 min at 25° C. After stirring the mixture for 30 minutes, was added a solution of N,N-dimethylpropane-1,3-diamine (3.62 g, 35.45 mmol) in DMF (10 mL) over a period of 20 min at 25° C. and stirred for 40 minutes. After completion of the reaction, water (100 mL) was charged at 25° C. over a period of 1 h. The resulting suspension was stirred for 4 h and filtered. The cake was washed with water (50 mL) and dried under vacuum at 50° C. for 12 h to afford the title product as a light brown solid (10 g, 83%); $^1$H NMR (400 MHz, CDCl$_3$) δ 9.36 (bs, 1 H), 8.87 (s, 1 H), 7.82 (d, J=7.53 Hz, 1 H), 7.76 (t, J=7.78Hz, 1 H), 7.49 (s, 1 H), 7.41 (d, J=8.03 Hz, 1 H), 3.43 (q, J=6.86 Hz, 2 H), 2.30-2.35 (m, 2 H), 2.29 (s, 3 H), 2.20 (s, 6 H), 1.74 (p, J=7.28 Hz, 2 H); LCMS$^m$/z: 508 [M$^+$].

LC (method C) rt=2.9 min.

5-[1(4-cyanophenyl)-1H-pyrazol-5-yl]-N-[3-(dimethylamino)propyl]-6-methyl-2-oxo-1-[3-(trifluoromethyl)phenyl]-1,2-dihydropyridine-3-carboxamide

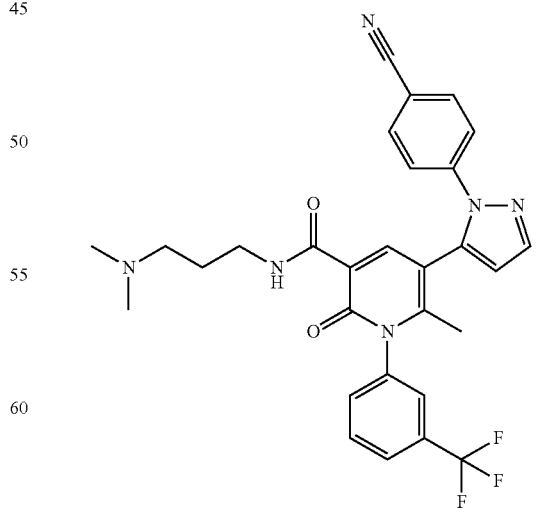

A mixture of N-[3-(dimethylamino)propyl]-5-iodo-6-methyl-2-oxo-1-[3-(trifluoromethyl)phenyl]-1,2-dihydropyridine-3-carboxamide (10 g, 19.71 mmol), 4-(5-(4,4,5,5-tetramethyl-1,3,2-dioxaborolan-2-yl)-1H-pyrazol-1-yl)benzonitrile (8.9 g, 29.55 mmol), water (0.71 g), N,N-dimethylformamide (100 mL) and diisopropylethylamine (7.64 g, 59.14 mmol) was purged with nitrogen for 10 minutes. To the above mixture was charged 1,1'-bis(di-tert-butylphosphino) ferrocene palladium dichloride ("Pd-118" ex. Johnson Matthey, 642.38 mg, 985.62 moles) and the mixture heated to 40° C. for 12 h. The reaction mixture was cooled to room temperature and was added to a mixture of isopropanol (100 mL) and water (200 mL). The resulting mixture was stirred for 18 h. The precipitate was filtered, washed with water (50 mL) and dried under vacuum at 50° C. for 12 h to afford the title product as a brown solid (6.2 g, 56%); $^1$H NMR (400 MHz, DMSO-$d_6$) δ 9.33 (t, J=5.77 Hz, 1 H), 8.07 (s, 1 H), 7.92-7.98 (m, 3 H), 7.91 (s, 1 H), 7.82-7.89 (m, 2 H), 7.72 (d, J=8.03 Hz, 1 H), 7.67 (d, J=8.53 Hz, 2 H), 6.73 (d, J=1.51 Hz, 1 H), 3.26 (q, J=6.86 Hz, 2 H), 2.25 (t, J=6.78 Hz, 2 H), 2.13 (s, 6 H), 1.75 (s, 3 H), 1.59 (p, J=7.03 Hz, 2 H); LCMS$^m$/z: 549 [M$^+$]

LC (method C) rt=3.1 min
Intermediate A:

Ethyl 5-(1-(4-cyanophenyl)-1H-pyrazol-5-yl)-6-methyl-2-oxo-1-(3-(trifluoromethyl)phenyl)-1,2-dihydropyridine-3-carboxylate

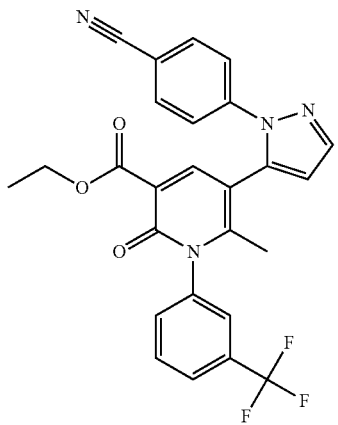 [SMILES: CCOC(=O)c1cc(-c2ccnn2-c2ccc(C#N)cc2)c(C)n(-c2cccc(C(F)(F)F)c2)c1=O]

Ethyl 5-iodo-6-methyl-2-oxo-1-(3-trifluoromethylphenyl)-1,2-dihydro-pyridine-3-carboxylate (synthesised according to WO2005/026123, Example 63 (b)) (9.02 g, 20 mmol), 4-(5-(4,4,5,5-tetramethyl-1,3,2-dioxaborolan-2-yl)-1H-pyrazol-1-yl)benzonitrile (synthesised according to WO2009/061271, Example 1 intermediate) (8.85 g, 30.00 mmol), potassium hydrogenphosphate trihydrate (13.69 g, 60.00 mmol) and 1,1'-bis(di-tert-butylphosphino) ferrocene palladium dichloride (0.918 g, 1.40 mmol) were suspended in DMF (100 mL) in a 250 mL round-bottomed flask and the mixture was purged with argon. Then 1,1'''-bis(di-tert-butylphosphino) ferrocene palladium dichloride (0.918 g, 1.40 mmol) was added and the reaction mixture was heated to 55° C. under vigorous stirring. After 30 and 90 min more 4-(5-(4,4,5,5-tetramethyl-1,3,2-dioxaborolan-2-yl)-1H-pyrazol-1-yl)benzonitrile (1.4 g, 4.74 mmol and 2.5 g, 8.47 mmol) was added.

After 3 h the reaction mixture was cooled to ambient, poured into ice/water (800mL) and the suspension stirred for 2 h. An oily product was obtained. The water was decanted and the gummy residue was washed with water.

The residue was dissolved in small amounts of dichloromethane and chromatographed by column chromatography (SiO$_2$; EtOAc/heptane 1:2 to 3:2) as eluent afforded 9.45 g of the title compound product containing approx 10-20% deiodinated starting material.

The impure product was recrystallized from EtOH (50 mL) to afford Intermediate A (7.5 g, 76%) as a white solid; $^1$H NMR (399.988 MHz, CDCl$_3$) δ 1.36 (3H, t), 1.64 (3H, s), 4.36 (2H, q), 6.55 (1H, d), 7.26-7.30 (1H, m), 7.38 (1H, s), 7.52 (2H, dd), 7.68 (1H, t), 7.72-7.78 (3H, m), 7.83 (1H, d), 8.16 (1H, s); APCI-MS$^m$/z: 493 [M$^+$]

Human Neutrophil Elastase Quenched-FRET Assay

The assay uses Human Neutrophil Elastase (HNE) purified from serum (Calbiochem art. 324681; Ref Baugh, R. J. et al., 1976, Biochemistry. 15, 836-841). HNE was stored in 50 mM sodium acetate (NaOAc), 500 mM sodium chloride (NaCl), pH 5.5 with added 50% glycerol at −20° C. The protease substrate used was Elastase Substrate V Fluorogenic, MeO-Suc-AAPV-AMC (Calbiochem art. 324740; Ref Castillo, M. J. et al., 1979, Anal. Biochem. 99, 53-64). The substrate was stored in dimethyl sulphoxide (DMSO) at −20° C. The assay additions were as follows: Test compounds and controls were added to black 384-well flat-bottom plates (Greiner 781076), 0.2 μL in 100% DMSO, followed by 10 μL HNE in assay buffer with 0.01% Triton (trade mark) X-100 detergent. The assay buffer constitution was: 100 mM Tris(hydroxymethyl) aminomethane (TRIS) (pH 7.5) and 500 mM NaCl. The enzyme and the compounds were incubated at room temperature for 15 minutes. Then 10 μL substrate in assay buffer was added. The assay was incubated for 90 minutes at room temperature. The concentrations of HNE enzyme and substrate during the incubation were 0.17 nM and 100 μM, respectively. The assay was then stopped by adding 20 μl stop solution (140 mM acetic acid, 200 mM sodium monochloroacetate, 60 mM sodium acetate, pH 4.3). Fluorescence was measured on a Wallac EnVision 2102 Multilabel Reader instrument at settings: Excitation 380 nm, Emission 460 nm. IC$_{50}$ values were determined using Xlfit curve fitting using model 203. When tested in the above screen, the compounds of the Examples gave IC$_{50}$ values for inhibition of human neutrophil elastase activity of less than 5 μM (micromolar), suitably less than 1 μM indicating that the compounds of the invention are expected to possess useful therapeutic properties. Specimen results are shown in the following Table in which the IC$_{50}$ value represents the geomean of the IC$_{50}$ values measured for a particular compound and "n" refers to the number of times the compound was tested:

| Compound | Inhibition of Human Neutrophil Elastase IC$_{50}$ (nanomolar, nM) |
|---|---|
| Example 1 | 0.949 (n = 2) |
| Example 2 | 0.771 (n = 2) |
| Example 3 | 1.05 (n = 2) |
| Example 4 | 0.934 (n = 2) |
| Example 5 | 0.971 (n = 2) |
| Example 6 | 3.48 (n = 2) |
| Example 7 | 0.57 (n = 2) |
| Example 9a | 1.1 (n = 4) |

The invention claimed is:
1. The compound 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium Y;
wherein Y represents a pharmaceutically acceptable anion.

2. The compound as defined in claim 1 which is 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate.

3. A pharmaceutical composition comprising a compound as claimed in claim 1 in association with a pharmaceutically acceptable adjuvant, diluent or carrier.

4. The compound as defined in claim 2 which is 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form A, characterized in that said Form A has an X-ray powder diffraction pattern with specific peaks at 4.3, 11.5 and 23.1°2θ when measured using CuKα1 radiation.

5. The compound as defined in claim 2 which is 3-(5-(1-(4-cyanophenyl)-1H-pyrazol-5-yl)-6-methyl-2-oxo-1-(3-(trifluoromethyl)phenyl)-1,2-dihydropyridine-3-carboxamido)-N,N,N-trimethylpropan-1-aminium benzenesulfonate Form B, characterized in that said Form B has an X-ray powder diffraction pattern with specific peaks at 5.8, 7.5 and 17.2°2θ when measured using CuKα1 radiation.

\* \* \* \* \*

UNITED STATES PATENT AND TRADEMARK OFFICE
CERTIFICATE OF CORRECTION

| | | |
|---|---|---|
| PATENT NO. | : 8,436,024 B2 | Page 1 of 1 |
| APPLICATION NO. | : 12/895995 | |
| DATED | : May 7, 2013 | |
| INVENTOR(S) | : Murugan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 53 days.

Signed and Sealed this
Sixth Day of January, 2015

Michelle K. Lee
*Deputy Director of the United States Patent and Trademark Office*